(12) United States Patent
Waycuilis

(10) Patent No.: US 7,880,041 B2
(45) Date of Patent: Feb. 1, 2011

(54) PROCESS FOR CONVERTING GASEOUS ALKANES TO LIQUID HYDROCARBONS

(75) Inventor: John J. Waycuilis, Cypress, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 693 days.

(21) Appl. No.: 11/778,479

(22) Filed: Jul. 16, 2007

(65) Prior Publication Data

US 2008/0171898 A1     Jul. 17, 2008

Related U.S. Application Data

(63) Continuation of application No. 10/826,885, filed on Apr. 16, 2004, now Pat. No. 7,244,867.

(51) Int. Cl.
*C10L 1/04*     (2006.01)
*C10L 1/06*     (2006.01)

(52) U.S. Cl. .................. 585/24; 585/14; 585/16; 44/300

(58) Field of Classification Search ............ 585/14, 585/24; 44/300
See application file for complete search history.

(56) References Cited

U.S. PATENT DOCUMENTS

| | | | |
|---|---|---|---|
| 2,168,260 A | 8/1939 | Heisel et al. |
| 2,246,082 A | 6/1941 | Vaughan et al. |
| 2,488,083 A | 11/1949 | Gorin et al. |
| 2,536,457 A | 1/1951 | Mugdan |
| 2,677,598 A | 5/1954 | Crummett et al. |
| 2,941,014 A | 6/1960 | Rothweiler et al. |
| 3,076,784 A | 2/1963 | Schulte-Huermann et al. |
| 3,172,915 A | 3/1965 | Borkowski et al. |
| 3,246,043 A | 4/1966 | Rosset et al. |
| 3,273,964 A | 9/1966 | Rosset |
| 3,294,846 A | 12/1966 | Livak et al. |

(Continued)

FOREIGN PATENT DOCUMENTS

BR     0210054     8/2004

(Continued)

OTHER PUBLICATIONS

Olah et al.; Hydrocarbons Through Methane Derivatives; Hydrocarbon Chemistry 2nd Edition; 2003; John Wiley & Sons, Inc.; pp. 123, 149, and 153.

(Continued)

*Primary Examiner*—Ellen M McAvoy
(74) *Attorney, Agent, or Firm*—Jack E. Ebel

(57) ABSTRACT

A process for converting gaseous alkanes to liquid hydrocarbons wherein a gaseous feed containing alkanes is reacted with a dry bromine vapor to form alkyl bromides and hydrobromic acid vapor. The mixture of alkyl bromides and hydrobromic acid are then reacted over a synthetic crystalline alumino-silicate catalyst, such as a ZSM-5 zeolite, at a temperature of from about 150° C. to about 400° C. so as to form higher molecular weight hydrocarbons and hydrobromic acid vapor. Hydrobromic acid vapor is removed from the higher molecular weight hydrocarbons. A portion of the propane and butane is removed from the higher molecular weight hydrocarbons and reacted with the mixture of alkyl bromides and hydrobromic acid over the synthetic crystalline aluminosilicate catalyst to form $C_{5+}$ hydrocarbons.

37 Claims, 6 Drawing Sheets

U.S. PATENT DOCUMENTS

| | | |
|---|---|---|
| 3,310,380 A | 3/1967 | Lester |
| 3,346,340 A | 10/1967 | Louvar et al. |
| 3,353,916 A | 11/1967 | Lester |
| 3,353,919 A | 11/1967 | Stockman |
| 3,496,242 A | 2/1970 | Berkowitz et al. |
| 3,562,321 A | 2/1971 | Borkowski et al. |
| 3,598,876 A | 8/1971 | Bloch |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A * | 3/1979 | Kaeding et al. ............... 585/24 |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |

| | | | | | | |
|---|---|---|---|---|---|---|
| 4,634,800 A | 1/1987 | Withers, Jr. et al. | | 5,001,293 A | 3/1991 | Nubel et al. |
| 4,642,403 A | 2/1987 | Hyde et al. | | 5,004,847 A | 4/1991 | Beaver et al. |
| 4,642,404 A | 2/1987 | Shihabi | | 5,013,424 A | 5/1991 | James, Jr. et al. |
| 4,652,688 A | 3/1987 | Brophy et al. | | 5,013,793 A | 5/1991 | Wang et al. |
| 4,654,449 A | 3/1987 | Chang et al. | | 5,019,652 A | 5/1991 | Taylor et al. |
| 4,655,893 A | 4/1987 | Beale | | 5,026,934 A | 6/1991 | Bains et al. |
| 4,658,073 A | 4/1987 | Tabak | | 5,026,937 A | 6/1991 | Bricker |
| 4,658,077 A | 4/1987 | Kolts et al. | | 5,026,944 A | 6/1991 | Allenger et al. |
| 4,665,259 A | 5/1987 | Brazdil et al. | | 5,034,566 A | 7/1991 | Ishino et al. |
| 4,665,267 A | 5/1987 | Barri | | 5,043,502 A | 8/1991 | Martindale et al. |
| 4,665,270 A | 5/1987 | Brophy et al. | | 5,055,235 A | 10/1991 | Brackenridge et al. |
| 4,675,410 A | 6/1987 | Feitler et al. | | 5,055,625 A * | 10/1991 | Neidiffer et al. ............... 585/14 |
| 4,690,903 A | 9/1987 | Chen et al. | | 5,055,633 A | 10/1991 | Volles |
| 4,695,663 A | 9/1987 | Hall et al. | | 5,055,634 A | 10/1991 | Volles |
| 4,696,985 A | 9/1987 | Martin | | 5,059,744 A | 10/1991 | Harandi et al. |
| 4,704,488 A | 11/1987 | Devries et al. | | 5,068,478 A | 11/1991 | Miller et al. |
| 4,704,493 A | 11/1987 | Devires et al. | | 5,071,449 A | 12/1991 | Sircar |
| 4,709,108 A | 11/1987 | Devries et al. | | 5,071,815 A | 12/1991 | Wallace et al. |
| 4,720,600 A | 1/1988 | Beech, Jr. et al. | | 5,073,656 A | 12/1991 | Chafin et al. |
| 4,720,602 A | 1/1988 | Chu | | 5,073,657 A | 12/1991 | Warren |
| 4,724,275 A | 2/1988 | Hinnenkamp et al. | | 5,082,473 A | 1/1992 | Keefer |
| 4,735,747 A | 4/1988 | Ollivier et al. | | 5,082,816 A | 1/1992 | Teller et al. |
| 4,737,594 A | 4/1988 | Olah | | 5,085,674 A | 2/1992 | Leavitt |
| 4,748,013 A | 5/1988 | Saito et al. | | 5,087,779 A | 2/1992 | Nubel et al. |
| 4,769,504 A | 9/1988 | Noceti et al. | | 5,087,786 A | 2/1992 | Nubel et al. |
| 4,774,216 A | 9/1988 | Kolts et al. | | 5,087,787 A | 2/1992 | Kimble et al. |
| 4,775,462 A | 10/1988 | Imai et al. | | 5,093,533 A * | 3/1992 | Wilson ........................ 585/1 |
| 4,777,321 A | 10/1988 | Harandi et al. | | 5,093,542 A | 3/1992 | Gaffney |
| 4,781,733 A | 11/1988 | Babcock et al. | | 5,096,469 A | 3/1992 | Keefer |
| 4,783,566 A | 11/1988 | Kocal et al. | | 5,097,083 A | 3/1992 | Stauffer |
| 4,788,369 A | 11/1988 | Marsh et al. | | 5,099,084 A | 3/1992 | Stauffer |
| 4,788,377 A | 11/1988 | Chang et al. | | 5,105,045 A | 4/1992 | Kimble et al. |
| 4,792,642 A | 12/1988 | Rule et al. | | 5,105,046 A | 4/1992 | Washecheck |
| 4,795,732 A | 1/1989 | Barri | | 5,107,032 A | 4/1992 | Erb et al. |
| 4,795,737 A | 1/1989 | Rule et al. | | 5,107,051 A | 4/1992 | Pannell |
| 4,795,843 A | 1/1989 | Imai et al. | | 5,107,061 A | 4/1992 | Ou et al. |
| 4,795,848 A | 1/1989 | Teller et al. | | 5,108,579 A | 4/1992 | Casci |
| 4,804,797 A | 2/1989 | Minet et al. | | 5,118,899 A | 6/1992 | Kimble et al. |
| 4,804,800 A | 2/1989 | Bortinger et al. | | 5,120,332 A | 6/1992 | Wells |
| 4,808,763 A | 2/1989 | Shum | | 5,132,343 A | 7/1992 | Zwecker et al. |
| 4,814,527 A | 3/1989 | Diesen | | 5,138,112 A | 8/1992 | Gosling et al. |
| 4,814,532 A | 3/1989 | Yoshida et al. | | 5,139,991 A | 8/1992 | Taylor et al. |
| 4,814,535 A | 3/1989 | Yurchak | | 5,146,027 A | 9/1992 | Gaffney |
| 4,814,536 A | 3/1989 | Yuchak | | 5,157,189 A | 10/1992 | Karra |
| 4,849,562 A | 7/1989 | Buhs et al. | | 5,160,502 A | 11/1992 | Kimble et al. |
| 4,849,573 A | 7/1989 | Kaefing | | 5,166,452 A | 11/1992 | Gradl et al. |
| 4,851,602 A | 7/1989 | Harandi et al. | | 5,175,382 A | 12/1992 | Hebgen et al. |
| 4,851,606 A | 7/1989 | Ragonese et al. | | 5,178,748 A | 1/1993 | Casci et al. |
| 4,886,925 A | 12/1989 | Harandi | | 5,185,479 A | 2/1993 | Stauffer |
| 4,886,932 A | 12/1989 | Leyshon | | 5,188,725 A | 2/1993 | Harandi |
| 4,891,463 A | 1/1990 | Chu | | 5,191,142 A | 3/1993 | Marshall et al. |
| 4,895,995 A | 1/1990 | James, Jr. et al. | | 5,194,244 A | 3/1993 | Brownscombe et al. |
| 4,899,000 A | 2/1990 | Stauffer | | 5,202,506 A | 4/1993 | Kirchner et al. |
| 4,899,001 A | 2/1990 | Kalnes et al. | | 5,202,511 A | 4/1993 | Salinas, III et al. |
| 4,899,002 A | 2/1990 | Harandi et al. | | 5,208,402 A * | 5/1993 | Wilson ........................ 585/1 |
| 4,902,842 A | 2/1990 | Kalnes et al. | | 5,210,357 A | 5/1993 | Kolts et al. |
| 4,925,995 A | 5/1990 | Robschlager | | 5,215,648 A | 6/1993 | Zones et al. |
| 4,929,781 A | 5/1990 | James, Jr. et al. | | 5,223,471 A | 6/1993 | Washecheck |
| 4,939,310 A | 7/1990 | Wade | | 5,228,888 A | 7/1993 | Gmelin et al. |
| 4,939,311 A | 7/1990 | Washecheck et al. | | 5,233,113 A | 8/1993 | Periana et al. |
| 4,939,314 A | 7/1990 | Harandi et al. | | 5,237,115 A | 8/1993 | Makovec et al. |
| 4,945,175 A | 7/1990 | Hobbs et al. | | 5,243,098 A | 9/1993 | Miller et al. |
| 4,950,811 A | 8/1990 | Doussain et al. | | 5,243,114 A | 9/1993 | Johnson et al. |
| 4,950,822 A | 8/1990 | Dileo et al. | | 5,245,109 A | 9/1993 | Kaminsky et al. |
| 4,956,521 A | 9/1990 | Volles | | 5,254,772 A | 10/1993 | Dukat et al. |
| 4,962,252 A | 10/1990 | Wade | | 5,254,790 A | 10/1993 | Thomas et al. |
| 4,973,776 A | 11/1990 | Allenger et al. | | 5,264,635 A | 11/1993 | Le et al. |
| 4,973,786 A | 11/1990 | Karra | | 5,268,518 A | 12/1993 | West et al. |
| 4,982,024 A | 1/1991 | Lin et al. | | 5,276,226 A | 1/1994 | Horvath et al. |
| 4,982,041 A | 1/1991 | Campbell | | 5,276,240 A | 1/1994 | Timmons et al. |
| 4,988,660 A | 1/1991 | Campbell | | 5,276,242 A | 1/1994 | Wu |
| 4,990,696 A | 2/1991 | Stauffer | | 5,284,990 A | 2/1994 | Peterson et al. |
| 4,990,711 A | 2/1991 | Chen et al. | | 5,300,126 A | 4/1994 | Brown et al. |

| Patent | Date | Inventor |
|---|---|---|
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A * | 7/1998 | Riley .......................... 44/300 |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. et al. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |

| Patent | Date | Inventor |
|---|---|---|
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 * | 12/2002 | Briot et al. .................... 208/18 |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 * | 10/2005 | Yan et al. ....................... 585/14 |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Fernandez et al. |
| 7,037,358 B2 | 5/2006 | Babicki et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,064,238 B2 | 6/2006 | Ding et al. |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |

| | | | | | |
|---|---|---|---|---|---|
| 7,304,193 B1 | 12/2007 | Frey et al. | 2008/0188697 A1 | 8/2008 | Lorkovic |
| 7,342,144 B2 | 3/2008 | Kaizik et al. | 2008/0200740 A1 | 8/2008 | Waycuilis |
| 7,348,295 B2 | 3/2008 | Zones et al. | 2008/0275284 A1 | 11/2008 | Waycuilis |
| 7,348,464 B2 | 3/2008 | Waycuilis | 2009/0005620 A1 | 1/2009 | Waycuilis et al. |
| 7,357,904 B2 | 4/2008 | Zones et al. | 2009/0247796 A1 | 10/2009 | Waycuilis et al. |
| 7,361,794 B2 | 4/2008 | Grosso | 2009/0308759 A1 | 12/2009 | Waycuilis |
| 7,390,395 B2 | 6/2008 | Elomari | 2009/0312586 A1 | 12/2009 | Waycuilis et al. |
| 7,560,607 B2 | 7/2009 | Waycuilis | 2009/0326292 A1 | 12/2009 | Waycuilis |
| 7,674,941 B2 | 3/2010 | Waycuilis et al. | | | |

FOREIGN PATENT DOCUMENTS

| | | |
|---|---|---|
| 2002/0102672 A1 | 8/2002 | Mizrahi |
| 2002/0193649 A1 | 12/2002 | O'Rear et al. |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1 | 10/2007 | Gadewar et al. |
| 2007/0276168 A1 | 11/2007 | Garel |
| 2007/0284284 A1 | 12/2007 | Zones |
| 2008/0022717 A1 | 1/2008 | Yoshida et al. |
| 2008/0183022 A1 | 7/2008 | Waycuilis |

| | | |
|---|---|---|
| CA | 1099656 | 4/1981 |
| CA | 1101441 | 5/1981 |
| CA | 1202610 | 4/1986 |
| CA | 2447761 A1 | 11/2002 |
| CA | 2471295 A1 | 7/2003 |
| CA | 2542857 | 5/2005 |
| CA | 2236126 | 8/2006 |
| CA | 2203115 | 9/2006 |
| CA | 2510093 | 12/2006 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 7/1998 |
| EP | 1186591 A2 | 3/2002 |
| EP | 1253126 A1 | 10/2002 |
| EP | 1312411 A2 | 5/2003 |
| EP | 1395536 | 3/2004 |
| EP | 1404636 | 4/2004 |
| EP | 1235769 B1 | 5/2004 |
| EP | 1435349 A2 | 7/2004 |
| EP | 1440939 A1 | 7/2004 |
| EP | 1474371 | 11/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 2/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 | 11/1961 |
| GB | 883256 A | 11/1961 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 A | 2/1972 |
| GB | 1446803 | 8/1976 |
| GB | 1542112 | 3/1979 |

| | | | |
|---|---|---|---|
| GB | 2095243 A | 9/1982 | |
| GB | 2095245 A | 9/1982 | |
| GB | 2095249 A | 9/1982 | |
| GB | 2116546 A | 9/1982 | |
| GB | 2120249 A | 11/1983 | |
| GB | 2185754 A | 7/1987 | |
| GB | 2191214 A | 12/1987 | |
| JP | 2004-529189 | 9/2004 | |
| SU | 694483 A1 | 10/1979 | |
| WO | 83/00859 | 3/1983 | |
| WO | 85/04863 | 11/1985 | |
| WO | 85/04867 | 11/1985 | |
| WO | 90/08120 | 7/1990 | |
| WO | 90/08752 | 8/1990 | |
| WO | 91/18856 | 12/1991 | |
| WO | 92/03401 | 3/1992 | |
| WO | 92/12946 | 8/1992 | |
| WO | 93/16798 | 9/1993 | |
| WO | 96/22263 | 7/1996 | |
| WO | 97/44302 | 11/1997 | |
| WO | 98/12165 | 3/1998 | |
| WO | 99/07443 | 2/1999 | |
| WO | 00/07718 A1 | 2/2000 | |
| WO | 00/09261 A1 | 2/2000 | |
| WO | 01/14300 A1 | 3/2001 | |
| WO | 01/38275 A1 | 5/2001 | |
| WO | 01/44149 A1 | 6/2001 | |
| WO | 02/094749 A1 | 11/2002 | |
| WO | 02/094750 A1 | 11/2002 | |
| WO | 02/094751 A2 | 11/2002 | |
| WO | 02/094752 A1 | 11/2002 | |
| WO | 03/000635 A1 | 1/2003 | |
| WO | 03/002251 A2 | 1/2003 | |
| WO | 03/018524 A1 | 3/2003 | |
| WO | 03/020676 A1 | 3/2003 | |
| WO | 03/022827 A1 | 3/2003 | |
| WO | 03/043575 A2 | 5/2003 | |
| WO | 03/051813 A1 | 6/2003 | |
| WO | 03/062143 A1 | 7/2003 | |
| WO | 03/062172 A2 | 7/2003 | |
| WO | 03/078366 A1 | 9/2003 | |
| WO | 2004/018093 A2 | 3/2004 | |
| WO | 2004/067487 A2 | 8/2004 | |
| WO | 2005/014168 A1 | 2/2005 | |
| WO | 2005/019143 A1 | 3/2005 | |
| WO | 2005/021468 A1 | 3/2005 | |
| WO | 2005/035121 A2 | 4/2005 | |
| WO | 2005/037758 A1 | 4/2005 | |
| WO | 2005/054120 A2 | 6/2005 | |
| WO | 2005/056525 A2 | 6/2005 | |
| WO | 2005/058782 A1 | 6/2005 | |
| WO | 2005/090272 A1 | 9/2005 | |
| WO | 2005/095310 A2 | 10/2005 | |
| WO | 2005/105709 A1 | 11/2005 | |
| WO | 2005/105715 A1 | 11/2005 | |
| WO | 2005/110953 A1 | 11/2005 | |
| WO | 2005104689 A2 | 11/2005 | |
| WO | 2005/113437 A1 | 12/2005 | |
| WO | 2005/113440 A1 | 12/2005 | |
| WO | 2006/007093 A1 | 1/2006 | |
| WO | 2006/015824 A1 | 2/2006 | |
| WO | 2006/019399 A2 | 2/2006 | |
| WO | 2006/020234 A1 | 2/2006 | |
| WO | 2006/036293 A1 | 4/2006 | |
| WO | 2006/039213 A1 | 4/2006 | |
| WO | 2006/039354 A2 | 4/2006 | |
| WO | 2006/043075 A1 | 4/2006 | |
| WO | 2006/053345 A1 | 5/2006 | |
| WO | 2006-067155 A2 | 6/2006 | |
| WO | 2006/067188 A1 | 6/2006 | |
| WO | 2006/067190 A1 | 6/2006 | |
| WO | 2006/067191 A1 | 6/2006 | |
| WO | 2006/067192 A1 | 6/2006 | |
| WO | 2006/067193 A1 | 6/2006 | |
| WO | 2006/069107 A2 | 6/2006 | |
| WO | 2006/071354 A1 | 7/2006 | |
| WO | 2006/076942 A1 | 7/2006 | |
| WO | 2006/083427 A2 | 8/2006 | |
| WO | 2006-100312 A2 | 9/2006 | |
| WO | 2006/104909 A2 | 10/2006 | |
| WO | 2006/104914 A1 | 10/2006 | |
| WO | 2006/111997 A1 | 10/2006 | |
| WO | 2006/113205 A2 | 10/2006 | |
| WO | 2006/118935 A2 | 11/2006 | |
| WO | 2007/001934 A2 | 1/2007 | |
| WO | 2007/017900 A2 | 2/2007 | |
| WO | 2007/044139 A1 | 4/2007 | |
| WO | 2007/046986 A2 | 4/2007 | |
| WO | 2007/050745 A1 | 5/2007 | |
| WO | 2007/071046 A1 | 6/2007 | |
| WO | 2007/079038 A2 | 7/2007 | |
| WO | 2007/091009 A2 | 8/2007 | |
| WO | 2007/094995 A2 | 8/2007 | |
| WO | 2007/107031 A1 | 9/2007 | |
| WO | 2007/111997 A2 | 10/2007 | |
| WO | 2007/114479 A1 | 10/2007 | |
| WO | 2007/125332 A1 | 11/2007 | |
| WO | 2007/130054 A1 | 11/2007 | |
| WO | 2007/130055 A1 | 11/2007 | |
| WO | 2007/141295 A1 | 12/2007 | |
| WO | 2007/142745 A1 | 12/2007 | |
| WO | 2008/036562 A1 | 3/2008 | |
| WO | 2008/036563 A2 | 3/2008 | |
| WO | 2008/106319 A1 | 9/2008 | |
| WO | 2008/157043 A1 | 12/2008 | |
| WO | 2008/157044 A1 | 12/2008 | |
| WO | 2008/157045 A1 | 12/2008 | |
| WO | 2008/157046 A1 | 12/2008 | |
| WO | 2008/157047 A1 | 12/2008 | |
| WO | 2009152403 A1 | 12/2009 | |
| WO | 2009152405 A1 | 12/2009 | |
| WO | 2009152408 A1 | 12/2009 | |

OTHER PUBLICATIONS

Rakoff et al.; Quimica Organica Fundamental; The Macmillan Company; 1966; pp. 58-63 and 76-77.
U.S. Office Action from U.S. Appl. No. 12/112,926 dated Jan. 7, 2010.
Abstract of EP0021497 (A1), Synthesis of polyoxyalkylene glycol monoalkyl ethers, Publication date: Jan. 7, 1981, Inventor: Gibson, esp@cenet database—worldwide.
U.S. Office Action from U.S. Appl. No. 10/365,346 dated Jun. 12, 2006.
U.S. Office Action from U.S. Appl. No. 10/893,418 dated Jun. 14, 2007.
U.S. Office Action from U.S. Appl. No. 10/893,418 dated Jan. 2, 2008.
U.S. Office Action from U.S. Appl. No. 11/091,130 dated Oct. 3, 2007.
Benizri et al., Study of the Liquid-Vapor Equilibrium in the Bromine-Hydrobromic Acid-Water System, Hydrogen Energy Vector, 1980, pp. 101-116.
Bradshaw et al., Production of Hydrobromic Acid from Bromine and Methane for Hydrogen Production, Proceedings of the 2001 DOE Hydrogen Program Review, NREL/CP-570-30535, 2001.
Motupally et al., Recycling Chlorine from Hydrogen Chloride, The Electrochemical Society Interface, Fall 2008, pp. 32-36.
Wauters et al., Electrolytic Membrane Recovery of Bromine from Waste Hydrogen Bromide Streams, AIChE Journal, Oct. 1998, vol. 44, No. 10, pp. 2144-2148.
Kirk-Othmer Encyclopedia of Chemical Technology, 4th Edition, vol. 1, A Wiley-Interscience Publication, John Wiley & Sons, 1991, pp. 946-997.
Adachi et al., Synthesis of Sialyl Lewis X Ganglioside Analogs Containing a Variable Length Spacer Between the Sugar and Lipophilic Moieties, J. Carbohydrate Chemistry, vol. 17, No. 4-5, 1998, pp. 595-607; XP009081720.

Bakker et al., An Exploratory Study of the Addition Reactions of Ethyleneglycol, 2-Chloroethanol and 1,3-Dichloro-2-Propanol to 1-Dodecene, J. Am. Oil Chem. Soc., vol. 44, No. 9, 1967, pp. 517-521; XP009081570.

Bouzide et al., Highly Selective Silver (I) Oxide Mediated Monoprotection of Symmetrical Diols, Tetrahedron Letters, Elsevier, vol. 38, No. 34, 1997, pp. 5945-5948; XP004094157.

Gibson et al., Phase-Transfer Synthesis of Monoalkyl Ethers of Oligoethylene Glycols, J. Org. Chem., vol. 45, No. 6, 1980, pp. 1095-1098; XP002427776.

Loiseau et al., Multigram Synthesis of Well-Defined Extended Bifunctional Polyethylene Glycol (PEG) Chains, J. Org. Chem., vol. 69, No. 3, 2004, pp. 639-647; XP002345040.

Mihai et al., Application of Bronsted-Type LFER in the Study of the Phospholipase C Mechanism, J. Am. Chem. Soc., vol. 125, No. 11, 2003, pp. 3236-3242; XP002427777.

Nishikawa et al., Ultrasonic Relaxations in Aqueous Solutions of Alcohols and the Balance between Hydrophobicity and Hydrophilicity of the Solutes, J. Phys. Chem., vol. 97, No. 14, 1993, pp. 3539-3544; XP002427775.

Prelog et al., Chirale 2,2'-Polyoxaalkano-9,9'-Spirobifluorene, Helvetica Chimica ACTA, vol. 62, No. 7, 1979, pp. 2285-2302; XP002030901.

Shimizu et al., Gas-Phase Electrolysis of Hydrobromic Acid Using PTFE-Bonded Carbon Electrode, Int. J. Hydrogen Energy, vol. 13, No. 6, pp. 345-349, 1988.

Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.

Whitesides et al., Nuclear Magnetic Resonance Spectroscopy. The Effect of Structure on Magnetic Nonequivalence Due to Molecular Asymmetry, J. Am. Chem. Soc., vol. 86, No. 13, 1964, pp. 2628-2634; XP002427774.

Combined International Search Report and Written Opinion Dated Apr. 17, 2007 for PCT/US2006/13394, in the name of GRT, Inc.

Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.

Abstract of JP2007061594, Method for decomposing organohalogen compound and mobile decomposition system, Publication date: Mar. 15, 2007, Inventor: Koichi et al., esp@cenet database—worldwide.

Abstract of JP2007099729, Method for producing alpha-methylstyrene or cumene, Publication date: Apr. 19, 2007, Inventor: Toshio, esp@cenet database—worldwide.

Abstract of RO119778, Process for preparing perchloroethylene, Publication date: Mar. 30, 2005, Inventor: Horia et al., esp@cenet database—worldwide.

Abstract of WO0105737, Method for preparing a carboxylic acid, Publication date: Jan. 25, 2001, Inventor: Pascal et al., esp@cenet database—worldwide.

Abstract of WO0105738, Method for preparing a carboxylic acid, Publication date: Jan. 25, 2001, Inventor: Pascal et al., esp@cenet database—worldwide.

Abstract of WO2004092099, Method for producing cyclic enols, Publication date: Oct. 28, 2004, Inventor: Marko et al., esp@cenet database—worldwide.

Abstract of WO2006063852, Electroluminescent polymers and use thereof, Publication date: Jun. 22, 2006, Inventor: Arne et al., esp@cenet database—worldwide.

Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.

Abstract of WO2007028761, Method for chlorinating alcohols, Publication date: Mar. 15, 2007, Inventor: Rohde et al., esp@cenet database—worldwide.

Abstract of WO2007128842, Catalytic transalkylation of dialkyl benzenes, Publication date: Nov. 15, 2007, Inventor: Goncalvesalmeida et al., esp@cenet database—worldwide.

Abstract of WO2007137566, Method for catalytic conversion of organic oxygenated compounds from biomaterials, Publication date: Dec. 6, 2007, Inventor: Reschetilowski, esp@cenet database—worldwide.

Abstract of WO9721656, Method for making fluoroalkanols, Publication date: Jun. 19, 1997, Inventor: Gillet, esp@cenet database—worldwide.

Abstract of WO9950213, Method for producing dialkyl ethers, Publication date: Oct. 7, 1999, Inventor: Falkowski Juergen et al., esp@cenet database—worldwide.

Abstract of WO2006076942, Method for the production of synthetic fuels from oxygenates, Publication date: Jul. 27, 2006, Inventor: Rothaemel et al., esp@cenet database—worldwide.

Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.

Abstract of EP0101337, Process for the production of methylene chloride, Publication date: Feb. 22, 1984, Inventor: Olah et al., esp@cenet database—worldwide.

Abstract of EP0407989, Method for the production of 1,1,1-trifluoro-2,2-dichloroethane by photochlorination, Publication date: Jan. 16, 1991, Inventor: Cremer et al., esp@cenet database—worldwide.

Abstract of EP0442258, Process for the preparation of a polyunsaturated olefin, Publication date: Aug. 21, 1991, Inventor: Gaudin et al., esp@cenet database—worldwide.

Abstract of EP0465294, Process for the preparation of unsaturated bromides, Publication date: Jan. 8, 1992, Inventor: Decaudin et al., esp@cenet database—worldwide.

Abstract of EP0549387, Synthesis of n-perfluorooctylbromide, Publication date: Jun. 30, 1993, Inventor: Drivon et al., esp@cenet database—worldwide.

Abstract of EP0850906, Process and apparatus for the etherification of olefinic hydrocarbon feedstocks, Publication date: Jul. 1, 1998, Inventor: Masson, esp@cenet database—worldwide.

Abstract of EP0858987, Process for the conversion of lighter alkanes to higher hydrocarbons, Publication date: Aug. 19, 1998, Inventor: Amariglio et al., esp@cenet database—worldwide.

Abstract of EP1404636, Integrated process for synthesizing alcohols and ethers from alkanes, Publication date: Apr. 7, 2004, Inventor: Zhou et al., esp@cenet database—worldwide.

Abstract of EP0235110, Process for the stabilization of silicalite catalysts, Publication date: Sep. 2, 1987, Inventor: Debras et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 1, 2007.

U.S. Appl. No. 60/487,364, filed Jul. 15, 2003, Lorkovic et al.

U.S. Appl. No. 60/559,844, filed Apr. 6, 2004, Sherman et al.

U.S. Appl. No. 60/765,115, filed Feb. 3, 2006, Gadewar et al.

JLM Technology Ltd.; "The Miller GLS Technology for Conversion of Light Hydrocarbons to Alcohols"; New Science for the Benefit of Humanity; May 31, 2000; pp. 1-10.

Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.

Taylor, Charles E.; "Conversion of Substituted Methanes Over ZSM-Catalysts"; 2000; pp. 3633-3638; Studies in Surface Science and Catalysis 130; Elsevier Science B.V.

ZSM-5 Catalyst; http://chemelab.ucsd.edu/methanol/memos/ZSM-5.html; Nov. 6, 2003; p. 1.

Final Report; "Abstract"; http://chemelab.ucsd.edu/methanol/memos/final.html; May 9, 2004; pp. 1-7.

Driscoll, Daniel J.; "Direct Methane Conversion"; Federal Energy Technology Center, U.S. Department of Energy; M970779; pp. 1-10.

Olah et al.; "Selective Monohalogenation of Methane over Supported Acid or Platinum Metal Catalysts and Hydrolysis of Methyl Halides . . . "; J. American Chemical Society 1985, vol. 107; 0002-7863/85/1507-7097$01.50/0; pp. 7097-7105.

Murray et al.; "Conversion of Methyl Halides to Hydrocarbons on Basic Zeolites: A Discovery by in Situ NMR"; J. American Chemical Society 1993, vol. 115; pp. 4732-4741.

Lorkovic et al.; "A Novel Integrated Process for the Functionalization of Methane and Ethane: Bromine as Mediator", Catalysis Today 98; 2004; pp. 317-322.

Lorkovic et al.; "C1 Oxidative Coupling via Bromine Activation and Tandem Catalytic Condensation over CaO/Zeolite Composites II . . . "; Catalysis Today 98; 2004; pp. 589-594.

Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.

Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.

Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.

Zhou, Xiao-Ping et al.; "An Integrated Process for Partial Oxidation of Alkanes"; Chem. Commun. 2003; The Royal Society of Chemistry 2003; pp. 2294-2295.

Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesoporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irena S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isao et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

U.S. Office Action from U.S. Appl. No. 12/112,926 dated Jan. 16, 2009.

U.S. Office Action from U.S. Appl. No. 12/112,926 dated Sep. 14, 2009.

Liu et al.; "Higher Hydrocarbons from Methane Condensation Mediated by HBr"; Journal of Molecular Catalysis A: Chemical 273; Elsevier B.V. 2007; pp. 14-20.

U.S. Office Action from U.S. Appl. No. 12/123,924 dated Mar. 19, 2010.

Abstract of BE812868, Aromatic hydrocarbons prodn. from chlorinated hydrocarbons, Publication date: Sep. 27, 1974, esp@cenet database—worldwide.

Abstract of BE814900, Volatile aramatic cpds. prodn., Publication date: Sep. 2, 1974, esp@cenet database—worldwide.

Abstract of CN1199039, Pentanol and its production process, Publication date: Nov. 18, 1998, Inventor: Kailun, esp@cenet database—worldwide.

Abstract of CN1210847, Process for producing low carbon alcohol by directly hydrating low carbon olefines, Publication date: Mar. 17, 1999, Inventor: Zhenguo et al., esp@cenet database—worldwide.

Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.
Abstract of CN1623969, Method for preparing 1, 4-benzene dimethanol, Publication date: Jun. 8, 2005, Inventor: Jiarong et al., esp@cenet database—worldwide.
Abstract of CN1657592, Method for converting oil to multiple energy fuel product, Publication date: Aug. 24, 2005, Inventor: Li, esp@cenet database—worldwide.
Abstract of CN1687316, Method for producing biologic diesel oil from rosin, Publication date: Oct. 26, 2005, Inventor: Jianchun et al., esp@cenet database—worldwide.
Abstract of CN1696248, Method for synthesizing biologic diesel oil based on ion liquid, Publication date: Nov. 16, 2005, Inventor: Sun, esp@cenet database—worldwide.
Abstract of CN1699516, Process for preparing bio-diesel-oil by using microalgae fat, Publication date: Nov. 23, 2005, Inventor: Miao, esp@cenet database—worldwide.
Abstract of CN1704392, Process for producing alkylbenzene, Publication date: Dec. 7, 2005, Inventor: Gao, esp@cenet database—worldwide.
Abstract of CN1724612, Biological diesel oil catalyst and method of synthesizing biological diesel oil using sai catalyst, Publication date: Jan. 25, 2006, Inventor: Gu, esp@cenet database—worldwide.
Abstract of CN1986737, Process of producing biodiesel oil with catering waste oil, Publication date: Jun. 27, 2007, Inventor: Chen, esp@cenet database—worldwide.
Abstract of CN100999680, Esterification reaction tech. of preparing biodiesel by waste oil, Publication date: Jul. 18, 2007, Inventor: Weiming, esp@cenet database—worldwide.
Abstract of CN101016229, Refining method for bromomeoamyl alcohol, Publication date: Aug. 15, 2007, Inventor: Tian, esp@cenet database—worldwide.
Abstract of DE3209964, Process for the preparation of chlorinated hydrocarbons, Publication date: Nov. 11, 1982, Inventor: Pyke et al., esp@cenet database—worldwide.
Abstract of DE3210196, Process for the preparation of a monochlorinated olefin, Publication date: Jan. 5, 1983, Inventor: Pyke et al., esp@cenet database—worldwide.
Abstract of DE3226028, Process for the preparation of monochlorinated olefin, Publication date: Feb. 3, 1983, Inventor: Pyke et al., esp@cenet database—worldwide.
Abstract of DE3334225, Process for the preparation of 1, 2-dichloroethane, Publication date: Apr. 4, 1985, Inventor: Hebgen et al., esp@cenet database—worldwide.
Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE4434823, Continuous prodn. of hydroxy-benzyl alkyl ether, Publication date: Apr. 4, 1996, Inventor: Stein et al., esp@cenet database—worldwide.
Abstract of FR2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR2883871, Preparing 1, 2-dichloroethane comprises cracking hydrocarbon to form mixture, sending mixture into storage reservoir, supplying mixture into chlorination and/or oxychlorination reactor, and separating 1, 2-dichloroethane from reactor, Publication date: Oct. 6, 2006, Inventor: Balthasart et al., esp@cenet database—worldwide.
Abstract of IT1255246, Process for the preparation of dinitrodiphenylmethanes, Publication date: Oct. 20, 1995, Applicant: Enichem Spa et al., esp@cenet database—worldwide.
Abstract of IT1255358, Process for the synthesis of 1, 4-butanediol, Publication date: Oct. 31, 1995, Inventor: Marco, esp@cenet database—worldwide.
Abstract of JP2142740, Production of fluoroalcohol, Publication date: May 31, 1990, Inventor: Tsutomu et al., esp@cenet database—worldwide.
Abstract of JP2144150, Chemical process and catalyst used therefore, Publication date: Jun. 1, 1990, Inventor: Deidamusu et al., esp@cenet database—worldwide.
Abstract of JP4305542, Production of halogenated hydrocarbon compounds, Publication date: Oct. 28, 1992, Inventor: Shinsuke et al., esp@cenet database—worldwide.
Abstract of JP6172225, Method for fluorinating halogenated hydrocarbon, Publication date: Jun. 21, 1994, Inventor: Takashi et al., esp@cenet database—worldwide.
Abstract of JP6206834, Production of tetrachloroethanes, Publication date: Jul. 26, 1994, Inventor: Toshiro et al., esp@cenet database—worldwide.
Abstract of JP8266888, Method for decomposing aromatic halogen compound, Publication date: Oct. 15, 1996, Inventor: Yuuji et al., esp@cenet database—worldwide.
Abstract of JP2001031605, Production of 3-hydroxy-1-cycloalkene, Publication date: Feb. 6, 2001, Inventor: Hideo et al, esp@cenet database—worldwide.
Abstract of JP2004075683, Method for producing optically active halogenohydroxypropyl compound and glycidyl compound, Publication date: Mar. 11, 2004, Inventor: Keisuke et al., esp@cenet database—worldwide.
Abstract of JP2004189655, Method for fluorinating with microwave, Publication date: Jul. 8, 2004, Inventor: Masaharu et al., esp@cenet database—worldwide.
Abstract of JP2005075798, Method for Producing adamantyl ester compound, Publication date: Mar. 24, 2005, Inventor: Norihiro et al., esp@cenet database—worldwide.
Abstract of JP2005082563, Method for producing 1, 3-adamantanediol, Publication date: Mar. 31, 2005, Inventor: Norihiro et al., esp@cenet database—worldwide.
Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP2005254092, Method of manufacturing alkynes, Publication date: Sep. 22, 2005, Inventor: Shirakawa Eiji, esp@cenet database—worldwide.
Abstract of JP2006151892, Preparation method of alcohol derivative, Publication date: Jun. 15, 2006, Inventor: Baba Akio et al., esp@cenet database—worldwide.
Abstract of JP2006152263, Organic-inorganic hybrid-type mesoporous material, method for producing the same, and solid catalyst, Publication date: Jun. 15, 2006, Inventor: Junko et al., esp@cenet database—worldwide.
Abstract of JP2006193473, Aryl polyadamantane derivative having carboxy or acid anhydride group and method for producing the same, Publication date: Jul. 27, 2006, Inventor: Yasuto et al., esp@cenet database—worldwide.
Abstract of JP2006231318, Phosphorus containing macromolecule immobilizing palladium catalyst and method for using the same, Publication date: Sep. 7, 2006, Inventor: Osamu et al., esp@cenet database—worldwide.
Abstract of JP2006263567, Optical resolution method of optical isomer and optical resolution device, Publication date: Oct. 5, 2006, Inventor: Yoshikazu et al., esp@cenet database—worldwide.
Abstract of JP2006265157, Method for catalytically activating silicated nucleating agent using phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 11, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

U.S. Office Action from U.S. Appl. No. 12/139,135 dated Nov. 24, 2010.

U.S. Office Action from U.S. Appl. No. 12/502,024 dated Oct. 26, 2010.

* cited by examiner

CH3Br CONVERSION & PRODUCT SELECTIVITY vs. TEMP
ZSM-5 CATALYST  GHSV 94 hr-1  CH3Br 27 mol%

◇ CH3Br CONV.
□ CH4 SELECT.
△ C3+ SELECT.

CH3Br CONVERSION & PRODUCT SELECTIVITY
over ZSM-5

≡ CH3Br CONV.
■ C2 SELECT.
▦ C3 SELECT.
▨ C4 SELECT.
▦ C5 SELECT.
▩ C6 SELECT.
□ C7+ SELECT.

PROCESS FOR CONVERTING GASEOUS ALKANES TO LIQUID HYDROCARBONS

REFERENCE TO RELATED PATENT APPLICATION

This application is a continuation of U.S. patent application Ser. No. 10/826,885, filed on Apr. 16, 2004, now U.S. Pat. No. 7,244,867 and titled "Process for Converting Gaseous Alkanes to Liquid Hydrocarbons".

BACKGROUND OF THE INVENTION

1. Field of the Invention

The present invention relates to a process for converting lower molecular weight, gaseous alkanes to liquid hydrocarbons useful for the production of fuels, and more particularly, to a process wherein a gas containing lower molecular weight alkanes is reacted with a dry bromine vapor to form alkyl bromides and hydrobromic acid which in turn are reacted over a crystalline alumino-silicate catalyst to form liquid hydrocarbons.

2. Description of Related Art

Natural gas which is primarily composed of methane and other light alkanes has been discovered in large quantities throughout the world. Many of the locales in which natural gas has been discovered are far from populated regions which have significant gas pipeline infrastructure or market demand for natural gas. Due to the low density of natural gas, transportation thereof in gaseous form by pipeline or as compressed gas in vessels is expensive. Accordingly, practical and economic limits exist to the distance over which natural gas may be transported in gaseous form. Cryogenic liquefaction of natural gas (LNG) is often used to more economically transport natural gas over large distances. However, this LNG process is expensive and there are limited regasification facilities in only a few countries that are equipped to import LNG.

Another use of methane found in natural gas is as feed to processes for the production of methanol. Methanol is made commercially via conversion of methane to synthesis gas (CO and $H_2$) at high temperatures (approximately 1000° C.) followed by synthesis at high pressures (approximately 100 atmospheres). There are several types of technologies for the production of synthesis gas (CO and $H_2$) from methane. Among these are steam-methane reforming (SMR), partial oxidation (POX), autothermal reforming (ATR), gas-heated reforming (GHR), and various combinations thereof. SMR and GHR operate at high pressures and temperatures, generally in excess of 600° C., and require expensive furnaces or reactors containing special heat and corrosion-resistant alloy tubes filled with expensive reforming catalyst. POX and ATR processes operate at high pressures and even higher temperatures, generally in excess of 1000° C. As there are no known practical metals or alloys that can operate at these temperatures, complex and costly refractory-lined reactors and high-pressure waste-heat boilers to quench & cool the synthesis gas effluent are required. Also, significant capital cost and large amounts of power are required for compression of oxygen or air to these high-pressure processes. Thus, due to the high temperatures and pressures involved, synthesis gas technology is expensive, resulting in a high cost methanol product which limits higher-value uses thereof, such as for chemical feedstocks and solvents. Furthermore production of synthesis gas is thermodynamically and chemically inefficient, producing large excesses of waste heat and unwanted carbon dioxide, which tends to lower the conversion efficiency of the overall process. Fischer-Tropsch Gas-to-Liquids (GTL) technology can also be used to convert synthesis gas to heavier liquid hydrocarbons, however investment cost for this process is even higher. In each case, the production of synthesis gas represents a large fraction of the capital costs for these methane conversion processes.

Numerous alternatives to the conventional production of synthesis gas as a route to methanol or synthetic liquid hydrocarbons have been proposed. However, to date, none of these alternatives has attained commercial status for various reasons. Some of the previous alternative prior-art methods, such as disclosed in U.S. Pat. Nos. 5,243,098 or 5,334,777 to Miller, teach reacting a lower alkane, such as methane, with a metallic halide to form a metalous halide and hydrohalic acid which are in turn reduced with magnesium oxide to form the corresponding alkanol. However, halogenation of methane using chlorine as the preferred halogen results in poor selectivity to the monomethyl halide ($CH_3Cl$), resulting in unwanted by-products such as $CH_2Cl_2$ and $CHCl_3$ which are difficult to convert or require severe limitation of conversion per pass and hence very high recycle rates. Furthermore, these processes require movement and fluidization of solid metal salts and/or oxides which requires significant power, causes erosion of equipment and generation of fine dust which must be recovered and recycled.

Other prior art processes propose the catalytic chlorination or bromination of methane as an alternative to generation of synthesis gas (CO and $H_2$). To improve the selectivity of a methane halogenation step in an overall process for the production of methanol, U.S. Pat. No. 5,998,679 to Miller teaches the use of bromine, generated by thermal decomposition of a metal bromide, to brominate alkanes in the presence of excess alkanes, which results in improved selectivity to mono-halogenated intermediates such as methyl bromide. To avoid the drawbacks of utilizing fluidized beds of moving solids, the process utilizes a liquid mixture of metal chloride hydrates and metal bromides. Processes described in U.S. Pat. Nos. 6,462,243 B1, 6,472,572 B1, and 6,525,230 to Grosso are capable of attaining higher selectivity to mono-halogenated intermediates by the use of catalytic bromination. The resulting alkyl bromides intermediates such as methyl bromide, are further converted to the corresponding alcohols and ethers, by reaction with metal oxides in circulating beds of moving solids, with the drawbacks that beds of moving solids entail as described above. Another embodiment of U.S. Pat. No. 6,525,230 avoids the drawbacks of moving beds by utilizing a zoned reactor vessel containing a fixed bed of metal oxide/metal bromide that is operated cyclically in four steps. Additional drawbacks to the processes described in these patents are the simultaneous feeding of hydrocarbon gas and oxygen or air to a reactor vessel increasing the potential of an explosive condition occurring within the equipment in the event of an unanticipated process upset or mechanical failure. Also, these processes tend to produce substantial quantities of dimethylether (DME) along with any alcohol. While DME is a promising potential diesel engine fuel substitute, as of yet, there currently exists no substantial market for DME, and hence an expensive additional catalytic process conversion step would be required to convert DME into a currently marketable product. Other processes have been proposed which circumvent the need for production of synthesis gas, such as U.S. Pat. Nos. 4,655,893 and 4,467,130 to Olah in which methane is catalytically condensed into gasoline-range hydrocarbons via catalytic condensation using superacid catalysts. However, none of these earlier alternative approaches have resulted in commercial processes.

It is known that substituted alkanes, in particular methanol, can be converted to olefins and gasoline boiling-range hydrocarbons over various forms of crystalline alumino-silicates also known as zeolites. In the Methanol to Gasoline (MTG) process, a shape selective zeolite catalyst, ZSM-5, is used to convert methanol to gasoline. Coal or methane gas can thus be converted to methanol using conventional technology and subsequently converted to gasoline. However due to the high cost of methanol production, and at current or projected prices for gasoline, the MTG process is not considered economically viable. Thus, a need exists for an economic process for the conversion of methane and other alkanes found in natural gas to useful liquid hydrocarbon products which, due to their higher density and value, are more economically transported thereby significantly aiding development of remote natural gas reserves. A further need exists for a process for converting alkanes present in natural gas which is relatively inexpensive, safe and simple in operation.

SUMMARY OF THE INVENTION

To achieve the foregoing and other objects, and in accordance with the purposes of the present invention, as embodied and broadly described herein, one characterization of the present invention is a process for converting gaseous alkanes to liquid hydrocarbons. A gaseous feed having lower molecular weight alkanes is reacted with bromine vapor to form alkyl bromides and hydrobromic acid which in turn are reacted in the presence of a synthetic crystalline alumino-silicate catalyst and at a temperature sufficient to form higher molecular weight hydrocarbons and hydrobromic acid vapor.

In another characterization of the present invention, a process is provided for converting gaseous lower molecular weight alkanes to liquid hydrocarbons wherein a gaseous feed containing lower molecular weight alkanes is reacted with bromine vapor to form alkyl bromides and hydrobromic acid. The alkyl bromides and hydrobromic acid are reacted in the presence of a synthetic crystalline alumino-silicate catalyst to form higher molecular weight hydrocarbons and hydrobromic acid vapor. Bromine is recovered from the hydrobromic acid vapor.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 2:
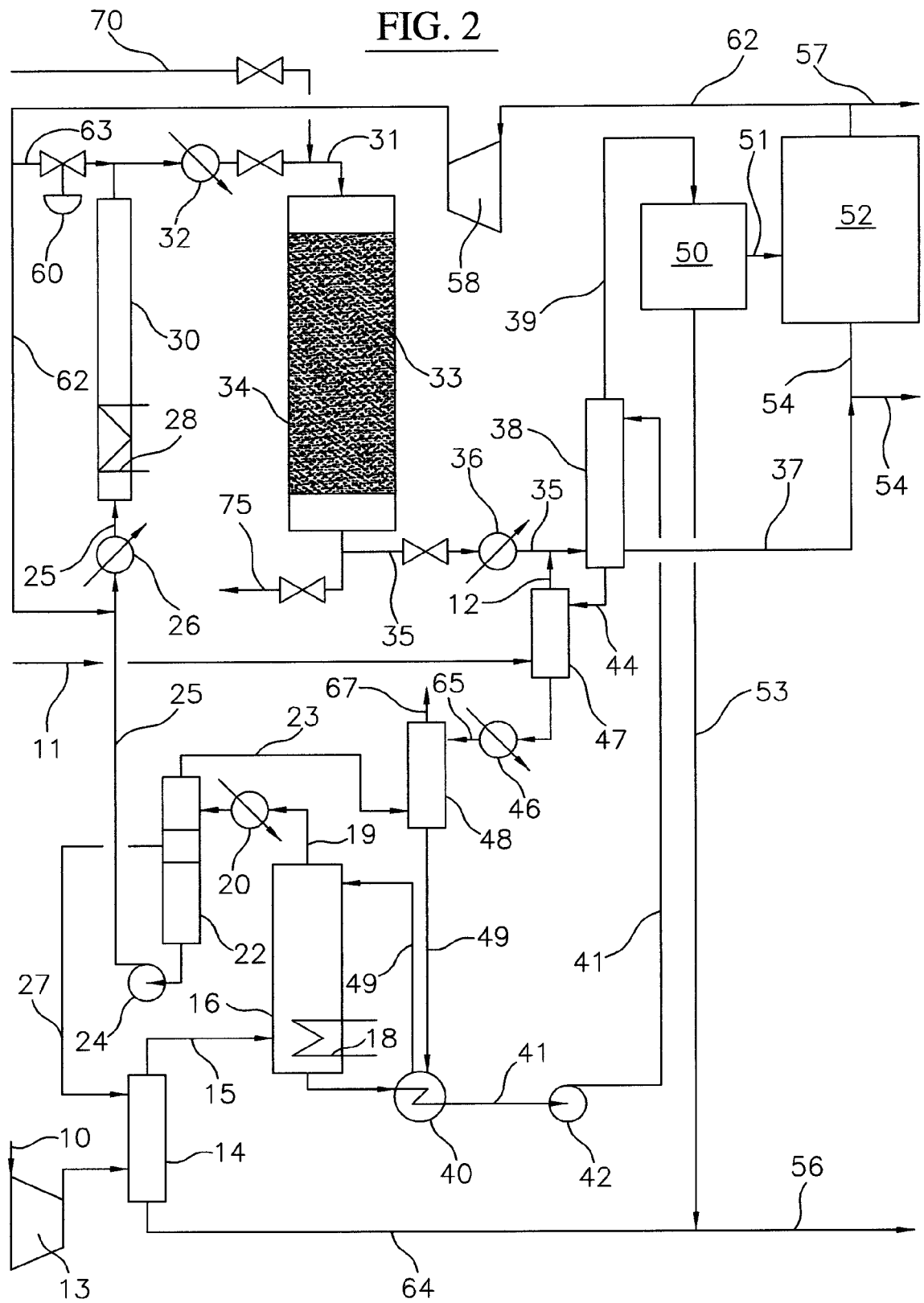
FIG. 2 is a schematic view of one embodiment of the process of the present invention.
Figure 3:
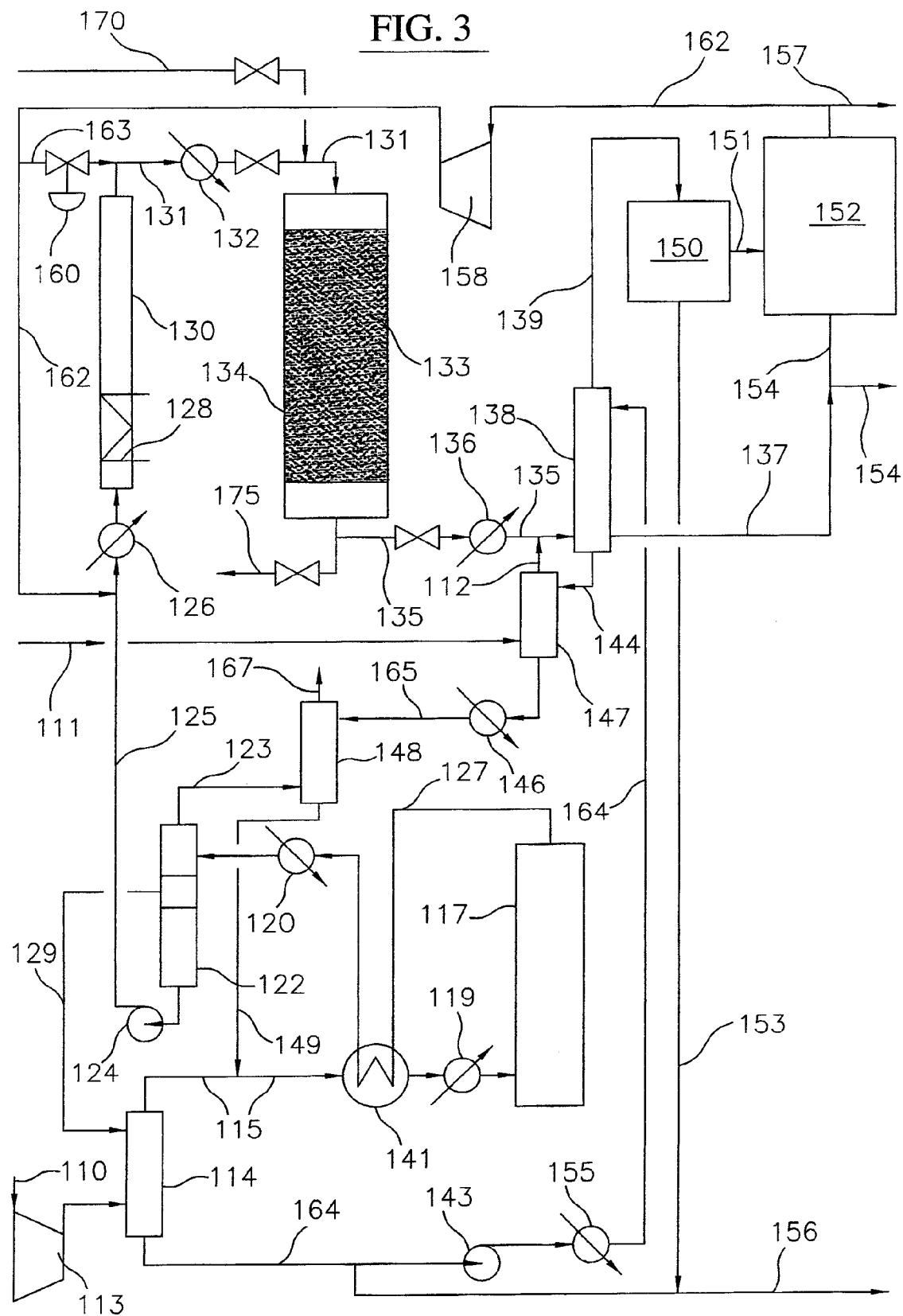
FIG. 3 is a schematic view of another embodiment of process of the present invention.

As utilized throughout this description, the term "lower molecular weight alkanes" refers to methane, ethane, propane, butane, pentane or mixtures thereof. As also utilized throughout this description, "alkyl bromides" refers to mono, di, and tri brominated alkanes. Also, the feed gas in lines 11 and 111 in the embodiments of the process of the present invention as illustrated in FIGS. 2 and 3, respectively, is preferably natural gas which may be treated to remove sulfur compounds and carbon dioxide. In any event, it is important to note that small amounts of carbon dioxide, e.g. less than about 2 mol %, can be tolerated in the feed gas to the process of the present invention.

Figure 1:
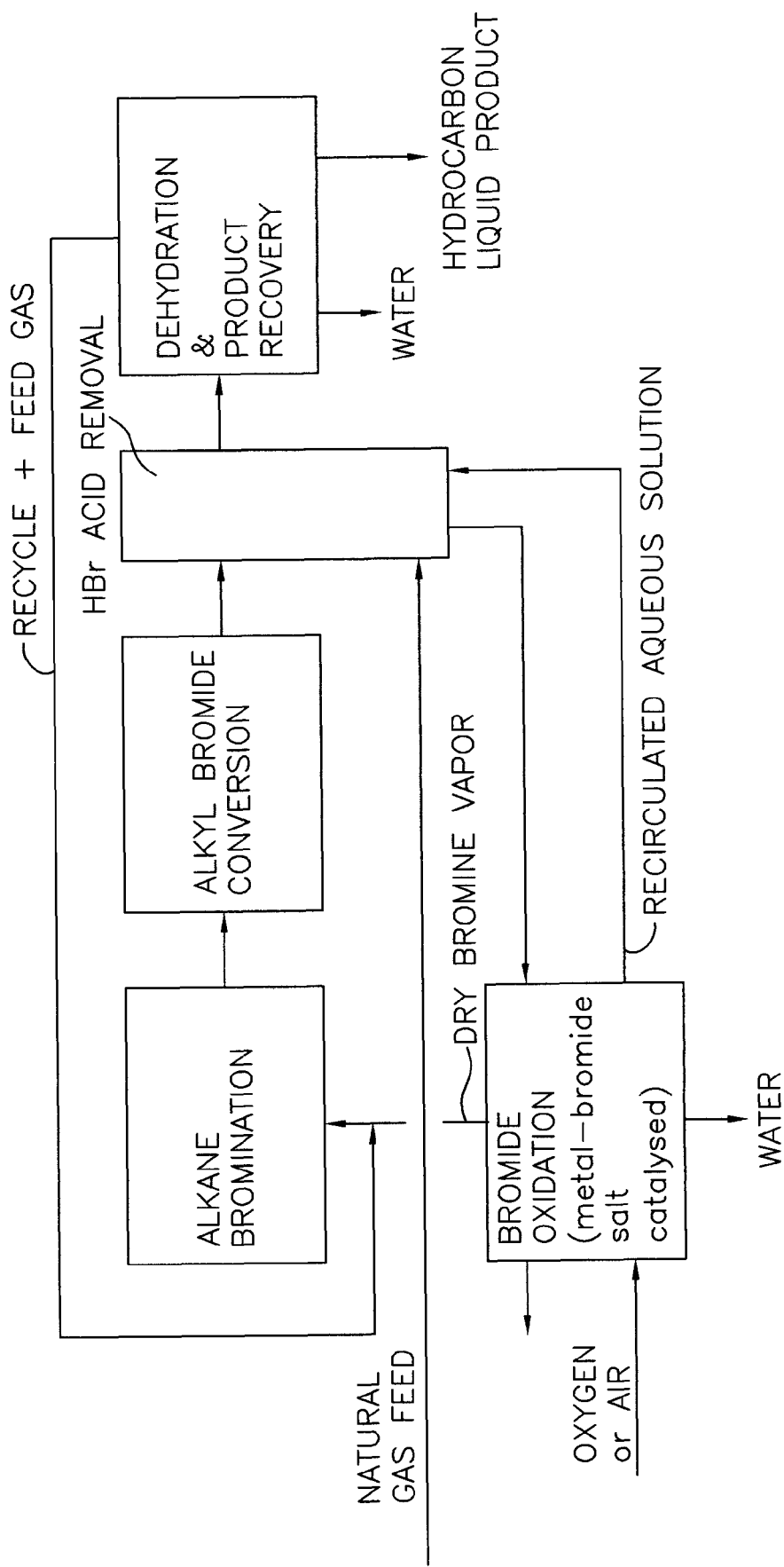
FIG. 1 is a simplified block flow diagram of the process of the present invention.

A block flow diagram generally depicting the process of the present invention is illustrated in FIG. 1, while specific embodiments of the process of the present invention are illustrated in FIGS. 2 and 3. Referring to FIG. 2, a gas stream containing lower molecular weight alkanes, comprised of a mixture of a feed gas plus a recycled gas stream at a pressure in the range of about 1 bar to about 30 bar, is transported or conveyed via line, pipe or conduit 62, mixed with dry bromine liquid transported via line 25 and pump 24, and passed to heat exchanger 26 wherein the liquid bromine is vaporized. The mixture of lower molecular weight alkanes and dry bromine vapor is fed to reactor 30. Preferably, the molar ratio of lower molecular weight alkanes to dry bromine vapor in the mixture introduced into reactor 30 is in excess of 2.5:1. Reactor 30 has an inlet pre-heater zone 28 which heats the mixture to a reaction initiation temperature in the range of about 250° C. to about 400° C.

In first reactor 30, the lower molecular weight alkanes are reacted exothermically with dry bromine vapor at a relatively low temperature in the range of about 250° C. to about 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

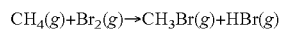

$$CH_4(g)+Br_2(g) \rightarrow CH_3Br(g)+HBr(g)$$

This reaction occurs with a significantly high degree of selectivity to methyl bromide. For example, in the case of bromination of methane with a methane to bromine ratio of about 4.5:1 selectivity to the mono-halogenated methyl bromide is in the range of 90 to 95%. Small amounts of dibromomethane and tribromomethane are also formed in the bromination reaction. Higher alkanes, such as ethane, propane and butane, are also readily bromoninated resulting in mono and multiple brominated species. If an alkane to bromine ratio of significantly less than about 2.5 to 1 is utilized, selectivity to methyl bromide substantially lower than 90% occurs and significant formation of undesirable carbon soot is observed. It has also been shown that other alkanes such as ethane and propane which may be present in the feed gas to the bromination reactor are readily brominated to form ethyl bromides and propyl bromides. Further, the dry bromine vapor that is feed into first reactor 30 is substantially water-free. Applicant has discovered that elimination of substantially all water vapor from the bromination step in first reactor 30 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor via line 31 and is partially cooled to a temperature in the range of about 150° C. to about 350° C. in heat exchanger 32 before flowing to a second reactor 34. In second reactor 34, the alkyl bromides are reacted exothermically at a temperature range of from about 150° C. to about 400° C., and a pressure in the range of about 1 to 30 bar, over a fixed bed 33 of crystalline aluminosilicate catalyst, preferably a zeolite catalyst, and most preferably a ZSM-5 zeolite catalyst. Although the zeolite catalyst is preferably used in the sodium or magnesium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W. Other zeolite catalysts having varying pore sizes and acidities, which are synthesized by varying the alumina-to-silica ratio may be used in the second reactor 34 as will be evident to a skilled artisan. In this reactor, the alkyl bromides are oligimerized to produce a mixture of higher molecular weight hydrocarbon products, primarily C3, C4 and C5+ gasoline-range and heavier hydrocarbon fractions, and additional hydrobromic acid vapor.

The temperature at which the second reactor 34 is operated is an important parameter in determining the selectivity of the oligimerization reaction to various higher molecular weight liquid hydrocarbon products. It is preferred to operate second reactor 34 at a temperature within the range of about 150° C. to 400° C. Temperatures above about 300° C. in the second reactor result in increased yields of light hydrocarbons, such as undesirable methane, whereas lower temperatures increase yields of heavier molecular weight hydrocarbon products. At the low end of the temperature range, with methyl bromide reacting over ZSM-5 zeolite at temperatures as low as 150° C. significant methyl bromide conversion on the order of 20% is noted, with a high selectivity towards $C_5+$ products. Also it is noted that methyl bromide appears to be more reactive over a lower temperature range relative to methyl chloride or other substituted methyl compounds such as methanol. Notably, in the case of the alkyl bromide reaction over the preferred zeolite ZSM-5 catalyst, cyclization reactions also occur such that the C7+ fractions are composed primarily of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$,—$C_3$ olefins are formed. At temperatures above about 425° C. almost complete conversion of methyl bromide to methane occurs. As a byproduct of the reaction, a small amount of carbon will build up on the catalyst over time during operation, causing a decline in catalyst activity over a range of several hundred hours, depending on the reaction conditions. It is believed that higher reaction temperatures favor the formation of carbon or coke and hence the rate of deactivation of the catalyst. Conversely, temperatures at the lower end of the range may also contribute to coking due to a reduced rate of adsorption of products. Hence, operating temperatures within the range of about 150° C. to 400° C., but preferably in the range of about 250° C. to about 350° C. in the second reactor 34 balance increased selectivity of the desired $C_5+$ products and lower rates of deactivation due to carbon formation, against higher conversion per pass, which minimizes the quantity of catalyst, recycle rates and equipment size required.

The catalyst may be periodically regenerated in situ, by isolating reactor 34 from the normal process flow, purging with an inert gas via line 70 at a pressure in a range from about 1 to about 5 bar at an elevated temperature in the range of about 400° C. to about 600° C. to remove unreacted material adsorbed on the catalyst insofar as is practical, and then subsequently oxidizing the deposited carbon to $CO_2$ by addition of air to reactor 34 via line 70 at a pressure in the range of about 1 bar to about 5 bar at an elevated temperature in the range of about 400° C. to about 600° C. Carbon dioxide and residual air is vented from reactor 34 via line 75 during the regeneration period.

The effluent which comprises the higher molecular weight hydrocarbon products and hydrobromic acid is withdrawn from the second reactor 34 via line 35 and is cooled to a temperature in the range of 0° C. to about 100° C. in exchanger 36 and combined with vapor effluent in line 12 from hydrocarbon stripper 47, which contains feed gas and residual hydrocarbon products stripped-out by contact with the feed gas in hydrocarbon stripper 47. The combined vapor mixture is passed to a scrubber 38 and contacted with an aqueous partially-oxidized metal bromide salt solution containing metal hydroxide and/or metal oxy-bromide species, that is transported to scrubber 38 via line 41. The preferred metal of the bromide salt is Cu(II), Zn(II) or Fe(III) as these are less expensive and readily oxidize at lower temperatures in the range of 120° C. to 180° C., allowing the use of fluor-polymer-lined equipment; although Co(II), Ni(II), Mn(II) or other transition-metals which form oxidizable bromide salts may be used in the process of the present invention. Alternatively, alkaline-earth metals which also form oxidizable bromide salts, such as Ca (II) or Mg(II) may be used. Any liquid hydrocarbon product condensed in scrubber 38 may be skimmed and withdrawn in line 37 and added to liquid hydrocarbon product exiting the product recovery unit 52 in line 54. Hydrobromic acid is dissolved in the aqueous solution and neutralized by the metal hydroxide and or metal oxy-bromide species to yield metal bromide salt in solution and water which is removed from the scrubber 38 via line 44.

The residual vapor phase containing the higher molecular weight hydrocarbon products that is removed as effluent from the scrubber 38 is forwarded via line 39 to dehydrator 50 to remove substantially all water via line 53 from the vapor stream. The water is then removed from the dehydrator 50 via line 53. The dried vapor stream containing the higher molecular weight hydrocarbon products is further passed via line 51 to product recovery unit 52 to recover propane and butane as desired, but primarily the $C_5+$ fraction as a liquid product in line 54. Any conventional method of dehydration and liquids recovery, such as solid-bed dessicant adsorption followed by refrigerated condensation, cryogenic expansion, or circulating absorption oil, as used to process natural gas or refinery gas streams, as will be evident to a skilled artisan, may be employed in the process of the present invention. The residual vapor effluent from product recovery unit 52 is then split into a purge stream 57 which may be utilized as fuel for the process and a recycled residual vapor which is compressed via compressor 58. The recycled residual vapor discharged from compressor 58 is split into two fractions. A first fraction that is equal to at least 2.5 times the feed gas molar volume is transported via line 62 and is combined with dry liquid bromine conveyed by pump 24, heated in exchanger 26 to vaporize the bromine and fed into first reactor 30. The second fraction is drawn off of line 62 via line 63 and is regulated by control valve 60, at a rate sufficient to dilute the alkyl bromide concentration to reactor 34 and absorb the heat of reaction such that reactor 34 is maintained at the selected operating temperature, preferably in the range of about 250° C. to about 350° C. in order to optimize conversion versus selectivity and to minimize the rate of catalyst deactivation due to the deposition of carbon. Thus, the dilution provided by the recycled vapor effluent permits selectivity of bromination in the first reactor 30 to be controlled in addition to moderating the temperature in second reactor 34.

Water containing metal bromide salt in solution which is removed from scrubber 38 via line 44 is passed to hydrocarbon stripper 47 wherein residual dissolved hydrocarbons are stripped from the aqueous phase by contact with incoming feed gas transported via line 11. The stripped aqueous solution is transported from hydrocarbon stripper 47 via line 65 and is cooled to a temperature in the range of about 0° C. to about 70° C. in heat exchanger 46 and then passed to absorber 48 in which residual bromine is recovered from vent stream in line 67. The aqueous solution effluent from scrubber 48 is transported via line 49 to a heat exchanger 40 to be preheated to a temperature in the range of about 100° C. to about 600° C., and most preferably in the range of about 120° C. to about 180° C. and passed to third reactor 16. Oxygen or air is delivered via line 10 by blower or compressor 13 at a pressure in the range of about ambient to about 5 bar to bromine stripper 14 to strip residual bromine from water which is removed from stripper 14 in line 64 and is combined with water stream 53 from dehydrator 50 to form water effluent stream in line 56 which is removed from the process. The oxygen or air leaving bromine stripper 14 is fed via line 15 to reactor 16 which operates at a pressure in the range of about ambient to about 5 bar and at a temperature in the range of about 100° C. to about 600° C., but most preferably in the range of about 120° C. to about 180° C. so as to oxidize an aqueous metal bromide salt solution to yield elemental bromine and metal hydroxide and or metal oxy-bromide species. As stated above, although Co(II), Ni(II), Mn(II) or other transition-metals which form oxidizable bromide salts can be used, the preferred metal of the bromide salt is Cu(II), Zn(II) or Fe(III) as these are less expensive and readily oxidize at lower temperatures in the range of about 120° C. to about 180° C., allowing the use of fluorpolymer-lined equipment. Alternatively, alkaline-earth metals which also form oxidizable bromide salts, such as Ca (II) or Mg(II) could be used.

Hydrobromic acid reacts with the metal hydroxide or metal oxy-bromide species so formed to once again yield the metal bromide salt and water. Heat exchanger 18 in reactor 16 supplies heat to vaporize water and bromine. Thus, the overall reactions result in the net oxidation of hydrobromic acid produced in first reactor 30 and second reactor 34 to elemental bromine and steam in the liquid phase catalyzed by the metal bromide/metal hydroxide operating in a catalytic cycle. In the case of the metal bromide being Cu(II)Br$_2$ the reactions are believed to be:

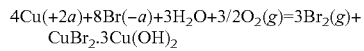

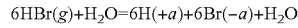

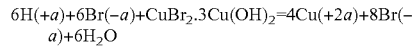

The elemental bromine and water and any residual oxygen or nitrogen (if air is utilized as the oxidant) leaving as vapor from the outlet of third reactor 16 via line 19, are cooled in condenser 20 at a temperature in the range of about 0° C. to about 70° C. and a pressure in the range of about ambient to 5 bar to condense the bromine and water and passed to three-phase separator 22. In three-phase separator 22, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus a substantially dry bromine vapor can be easily obtained by condensing liquid bromine and water, decanting water by simple physical separation and subsequently re-vaporizing liquid bromine.

Liquid bromine is pumped in line 25 from three-phase separator 22 via pump 24 to a pressure sufficient to mix with vapor stream 62. Thus bromine is recovered and recycled within the process. The residual oxygen or nitrogen and any residual bromine vapor which is not condensed exits three-phase separator 22 and is passed via line 23 to bromine scrubber 48, wherein residual bromine is recovered by solution into and by reaction with reduced metal bromides in the aqueous metal bromide solution stream 65. Water is removed from separator 22 via line 27 and introduced into stripper 14.

In another embodiment of the invention, referring to FIG. 3, a gas stream containing lower molecular weight alkanes, comprised of mixture of a feed gas plus a recycled gas stream at a pressure in the range of about 1 bar to about 30 bar, is transported or conveyed via line, pipe or conduit 162, mixed with dry bromine liquid transported via pump 124 and passed to heat exchanger 126 wherein the liquid bromine is vaporized. The mixture of lower molecular weight alkanes and dry bromine vapor is fed to reactor 130. Preferably, the molar ratio of lower molecular weight alkanes to dry bromine vapor in the mixture introduced into reactor 130 is in excess of 2.5:1. Reactor 130 has an inlet pre-heater zone 128 which heats the mixture to a reaction initiation temperature in the range of 250° C. to 400° C. In first reactor 130, the lower molecular weight alkanes are reacted exothermically with dry bromine vapor at a relatively low temperature in the range of 250° C. to 600° C., and at a pressure in the range of about 1 bar to about 30 bar to produce gaseous alkyl bromides and hydrobromic acid vapors. The upper limit of the operating temperature range is greater than the upper limit of the reaction initiation temperature range to which the feed mixture is heated due to the exothermic nature of the bromination reaction. In the case of methane, the formation of methyl bromide occurs in accordance with the following general reaction:

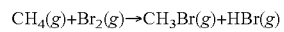

This reaction occurs with a significantly high degree of selectivity to methyl bromide. For example, in the case of bromine reacting with a molar excess of methane at a methane to bromine ratio of 4.5:1, selectivity to the mono-halogenated methyl bromide is in the range of 90 to 95%. Small amounts of dibromomethane and tribromomethane are also formed in the bromination reaction. Higher alkanes, such as ethane, propane and butane, are also readily brominated resulting in mono and multiple brominated species. If an alkane to bromine ratio of significantly less than 2.5 to 1 is utilized, selectivity to methyl bromide substantially lower than 90% occurs and significant formation of undesirable carbon soot is observed. It has also been shown that other alkanes such as ethane and propane which may be present in the feed gas to the bromination are readily brominated to form ethyl bromides and propyl bromides. Further, the dry bromine vapor that is feed into first reactor 130 is substantially water-free. Applicant has discovered that elimination of substantially all water vapor from the bromination step in first reactor 130 substantially eliminates the formation of unwanted carbon dioxide thereby increasing the selectivity of alkane bromination to alkyl bromides and eliminating the large amount of waste heat generated in the formation of carbon dioxide from alkanes.

The effluent that contains alkyl bromides and hydrobromic acid is withdrawn from the first reactor 130 via line 131 and is partially cooled to a temperature in the range of about 150° C. to 350° C. in heat exchanger 132 before flowing to a second reactor 134. In second reactor 134, the alkyl bromides are reacted exothermically at a temperature range of from about 150° C. to about 400° C., and a pressure in the range of about 1 bar to 30 bar, over a fixed bed of crystalline alumino-silicate catalyst, preferably a zeolite catalyst, and most preferably a ZSM-5 zeolite catalyst. Although the zeolite catalyst is preferably used in the sodium or magnesium form, the zeolite may also be modified by ion exchange with other alkali metal cations, such as Li, K or Cs, with alkali-earth metal cations, such as Mg, Ca, Sr or Ba, or with transition metal cations, such as Ni, Mn, V, W. Other zeolite catalysts having varying pore sizes and acidities, which are synthesized by varying the alumina-to-silica ratio may be used in the second reactor 134 as will be evident to a skilled artisan. In this reactor, the alkyl bromides are oligimerized to produce a mixture of higher molecular weight hydrocarbon products and additional hydrobromic acid vapor.

The temperature at which the second reactor 134 is operated is an important parameter in determining the selectivity of the oligimerization reaction to various higher molecular weight liquid hydrocarbon products. It is preferred to operate second reactor 134 at a temperature within the range of about 150° to 400°, but more preferably within the range of about 250 C to 350 C. Temperatures above about 300° C. in the second reactor result in increased yields of light hydrocarbons, such as undesirable methane, whereas lower temperatures increase yields of heavier molecular weight hydrocarbon products. At the low end of the temperature range, methyl bromide reacting over ZSM-5 zeolite at temperatures as low as 150° C. significant methyl bromide conversion on the order of 20% is noted, with a high selectivity towards $C_5+$ products. Notably, in the case of alkyl bromides reacting over the preferred ZSM-5 zeolite catalyst, cyclization reactions occur such that the $C_7+$ fractions produced contain a high percentage of substituted aromatics. At increasing temperatures approaching 300° C., methyl bromide conversion increases towards 90% or greater, however selectivity towards $C_5+$ products decreases and selectivity towards lighter products, particularly undesirable methane, increases. Surprisingly, very little ethane or $C_2$-$C_4$ olefin compounds are produced. At temperatures above about 425° C. almost complete conversion of methyl bromide to methane occurs. As a byproduct of the reaction, a small amount of carbon will build up on the catalyst over time during operation, causing a decline in catalyst activity over a range of several hundred hours, depending on the reaction conditions. It is believed that higher reaction temperatures favor the formation of carbon and hence rate of deactivation of the catalyst. Conversely, operation at the lower end of the temperature range may promote coking, likely to the reduced rate of desorption of hydrocarbon products. Hence, operating temperatures within the range of about 150° C. to 400° C. but more preferably in the range of about 250° C. to 350° C. in the second reactor 134 balance increased selectivity towards the desired products and lower rates of deactivation due to carbon formation, against higher conversion per pass, which minimizes the quantity of catalyst, recycle rates and equipment size required.

The catalyst may be periodically regenerated in situ, by isolating reactor 134 from the normal process flow, purging with an inert gas via line 170 at a pressure in the range of about 1 bar to about 5 bar and an elevated temperature in the range of 400° C. to 600° C. to remove unreacted material adsorbed on the catalyst insofar as is practical, and then subsequently oxidizing the deposited carbon to $CO_2$ by addition of air via line 170 to reactor 134 at a pressure in the range of about 1 bar to about 5 bar and an elevated temperature in the range of 400° C. to 600° C. Carbon dioxide and residual air are vented from reactor 134 via line 175 during the regeneration period.

The effluent which comprises the higher molecular weight hydrocarbon products and hydrobromic acid is withdrawn from the second reactor 134 via line 135, cooled to a temperature in the range of 0° C. to 100° C. in exchanger 136, and combined with vapor effluent in line 112 from hydrocarbon stripper 147. The mixture is then passed to a scrubber 138 and contacted with a stripped, recirculated water that is transported to scrubber 138 in line 164 by any suitable means, such as pump 143, and is cooled to a temperature in the range of 0° C. to 50° C. in heat exchanger 155. Any liquid hydrocarbon product condensed in scrubber 138 may be skimmed and withdrawn as stream 137 and added to liquid hydrocarbon product 154. Hydrobromic acid is dissolved in scrubber 138 in the aqueous solution which is removed from the scrubber 138 via line 144, and passed to hydrocarbon stripper 147 wherein residual hydrocarbons dissolved in the aqueous solution are stripped-out by contact with feed gas 111. The stripped aqueous phase effluent from hydrocarbon stripper 147 is cooled to a temperature in the range of 0° C. to 50° C. in heat exchanger 146 and then passed via line 165 to absorber 148 in which residual bromine is recovered from vent stream 167.

The residual vapor phase containing the higher molecular weight hydrocarbon products is removed as effluent from the scrubber 138 and forwarded to dehydrator 150 to remove substantially all water from the gas stream. The water is then removed from the dehydrator 150 via line 153. The dried gas stream containing the higher molecular weight hydrocarbon products is further passed via line 151 to product recovery unit 152 to recover $C_3$ and $C_4$ as desired, but primarily the $C_5+$ fraction as a liquid product in line 154. Any conventional method of dehydration and liquids recovery such as solid-bed dessicant adsorption followed by, for example, refrigerated condensation, cryogenic expansion, or circulating absorption oil, as used to process natural gas or refinery gas streams, as known to a skilled artisan, may be employed in the implementation of this invention. The residual vapor effluent from product recovery unit 152 is then split into a purge stream 157 that may be utilized as fuel for the process and a recycled residual vapor which is compressed via compressor 158. The recycled residual vapor discharged from compressor 158 is split into two fractions. A first fraction that is equal to at least 2.5 times the feed gas volume is transported via line 162, combined with the liquid bromine conveyed in line 125 and passed to heat exchanger 126 wherein the liquid bromine is vaporized and fed into first reactor 130. The second fraction which is drawn off line 162 via line 163 and is regulated by control valve 160, at a rate sufficient to dilute the alkyl bromide concentration to reactor 134 and absorb the heat of reaction such that reactor 134 is maintained at the selected operating temperature, preferably in the range of 250° C. to 350° C. in order to optimize conversion vs. selectivity and to minimize the rate of catalyst deactivation due to the deposition of carbon. Thus, the dilution provided by the recycled vapor effluent permits selectivity of bromination in the first reactor 130 to be controlled in addition to moderating the temperature in second reactor 134.

Oxygen or O$_2$-enriched air 110 is delivered via blower or compressor 113 at a pressure in the range of about ambient to about 5 bar to bromine stripper 114 to strip residual bromine from water which leaves stripper 114 via line 164 and is divided into two portions. The first portion of the stripped water is recycled via line 164, cooled in heat exchanger 155 to a temperature in the range of about 20° C. to about 50° C., and maintained at a pressure sufficient to enter scrubber 138 by any suitable means, such as pump 143. The portion of water that is recycled is selected such that the hydrobromic acid solution effluent removed from scrubber 138 via line 144 has a concentration in the range from about 10% to about 50% by weight hydrobromic acid, but more preferably in the range of about 30% to about 48% by weight to minimize the amount of water which must be vaporized in exchanger 141 and pre-heater 119. A second portion of water from stripper 114 is removed from line 164 and the process via line 156.

The dissolved hydrobromic acid that is contained in the aqueous solution effluent from scrubber 148 is transported via line 149 and is combined with the oxygen or O2-enriched air leaving bromine stripper 114 in line 115. The combined aqueous solution effluent and oxygen or O2-enriched air is passed to a first side of heat exchanger 141 and through preheater 119 wherein the mixture is preheated to a temperature in the range of about 100° C. to about 600° C. and most preferably in the range of about 120° C. to about 180° C. and passed to third reactor 117 that contains a metal bromide salt. The preferred metal of the bromide salt is Cu(II), Zn(II) or Fe(III) although Co(II), Ni(II), Mn(II) or other transition-metals which form oxidizable bromide salts can be used. Alternatively, alkaline-earth metals which also form oxidizable bromide salts, such as Ca(II) or Mg(II) could be used. The metal bromide salt in the oxidation reactor 117 can be utilized as a concentrated aqueous solution or preferably, the concentrated aqueous salt may be imbibed into a porous, high surface area, acid resistant inert support such as a silica gel. The oxidation reactor 117 operates at a pressure in the range of about ambient to about 5 bar and at a temperature in the range of about 100° C. to 600° C., but most preferably in the range of about 120° C. to 180° C.; therein, the metal bromide is oxidized by oxygen, yielding elemental bromine and metal hydroxide or metal oxy-bromide species or, metal oxides in the case of the supported metal bromide salt operated at higher temperatures and lower pressures at which water may primarily exist as a vapor. In either case, the hydrobromic acid reacts with the metal hydroxide, metal oxy-bromide or metal oxide species and is neutralized, restoring the metal bromide salt and yielding water. Thus, the overall reaction results in the net oxidation of hydrobromic acid produced in first reactor 130 and second reactor 134 to elemental bromine and steam, catalyzed by the metal bromide/metal hydroxide or metal oxide operating in a catalytic cycle. In the case of the metal bromide being Cu(II)Br$_2$ in an aqueous solution and operated in a pressure and temperature range in which water may exist as a liquid the reactions are believed to be:

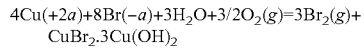

6HBr(g)+H$_2$O=6H(+a)+6Br(−a)+H$_2$O

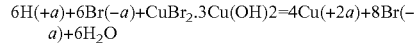

In the case of the metal bromide being Cu(II)Br$_2$ supported on an inert support and operated at higher temperature and lower pressure conditions at which water primarily exists as a vapor, the reactions are believed to be:

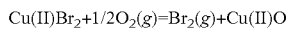

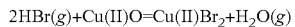

The elemental bromine and water and any residual oxygen or nitrogen (if enriched air is utilized as the oxidant) leaving as vapor from the outlet of third reactor 117, are cooled in the second side of exchanger 141 and condenser 120 to a temperature in the range of about 0° C. to about 70° C. wherein the bromine and water are condensed and passed to three-phase separator 122. In three-phase separator 122, since liquid water has a limited solubility for bromine, on the order of about 3% by weight, any additional bromine which is condensed forms a separate, denser liquid bromine phase. The liquid bromine phase, however, has a notably lower solubility for water, on the order of less than 0.1%. Thus, a substantially dry bromine vapor can be easily obtained by condensing liquid bromine and water, decanting water by simple physical separation and subsequently re-vaporizing liquid bromine.

Liquid bromine is pumped from three-phase separator 122 via pump 124 to a pressure sufficient to mix with vapor stream 162. Thus the bromine is recovered and recycled within the process. The residual enriched air or oxygen and any bromine vapor which is not condensed exits three-phase separator 122 and is passed via line 123 to bromine scrubber 148, wherein residual bromine is recovered by dissolution into hydrobromic acid solution stream conveyed to scrubber 148 via line 165. Water is removed from the three-phase separator 122 via line 129 and passed to stripper 114.

The following examples demonstrate the practice and utility of the present invention, but are not to be construed as limiting the scope thereof.

EXAMPLE 1

Various mixtures of dry bromine and methane are reacted homogeneously at temperatures in the range of 459° C. to 491° C. at a Gas Hourly Space Velocity (GHSV which is defined as the gas flow rate in standard liters per hour divided by the gross reactor catalyst-bed volume, including catalyst-bed porosity, in liters) of approximately 7200 hr$^{-1}$. The results of this example indicate that for molar ratios of methane to bromine greater than 4.5:1 selectivity to methyl bromide is in the range of 90 to 95%, with near-complete conversion of bromine.

EXAMPLE 2

Figure 7:
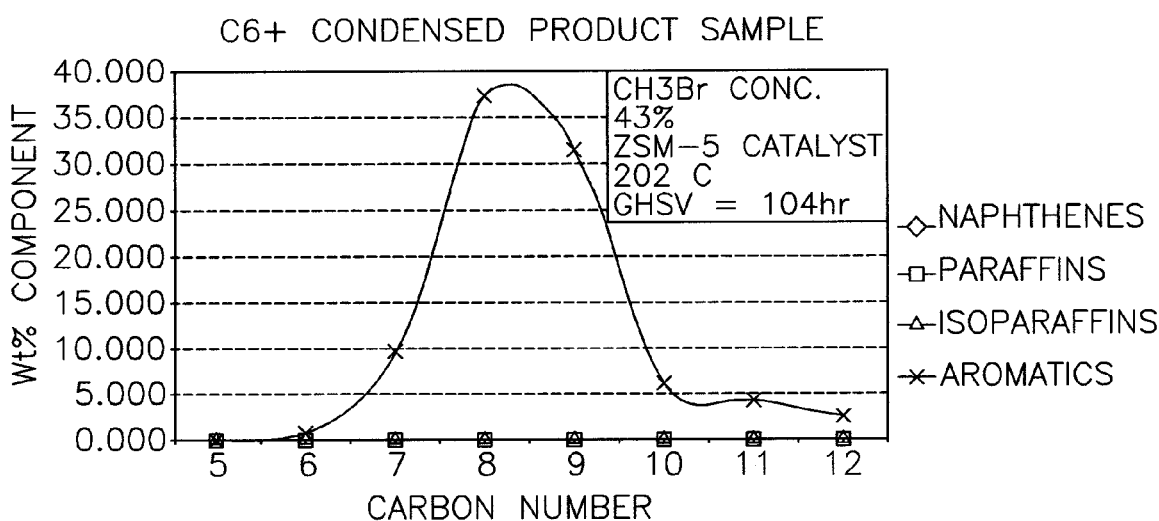
FIG. 7 is a graph of a Paraffinic Olefinic Napthenic and Aromatic (PONA) analysis of a typical condensed product sample of the process of the present invention.
Figure 8:
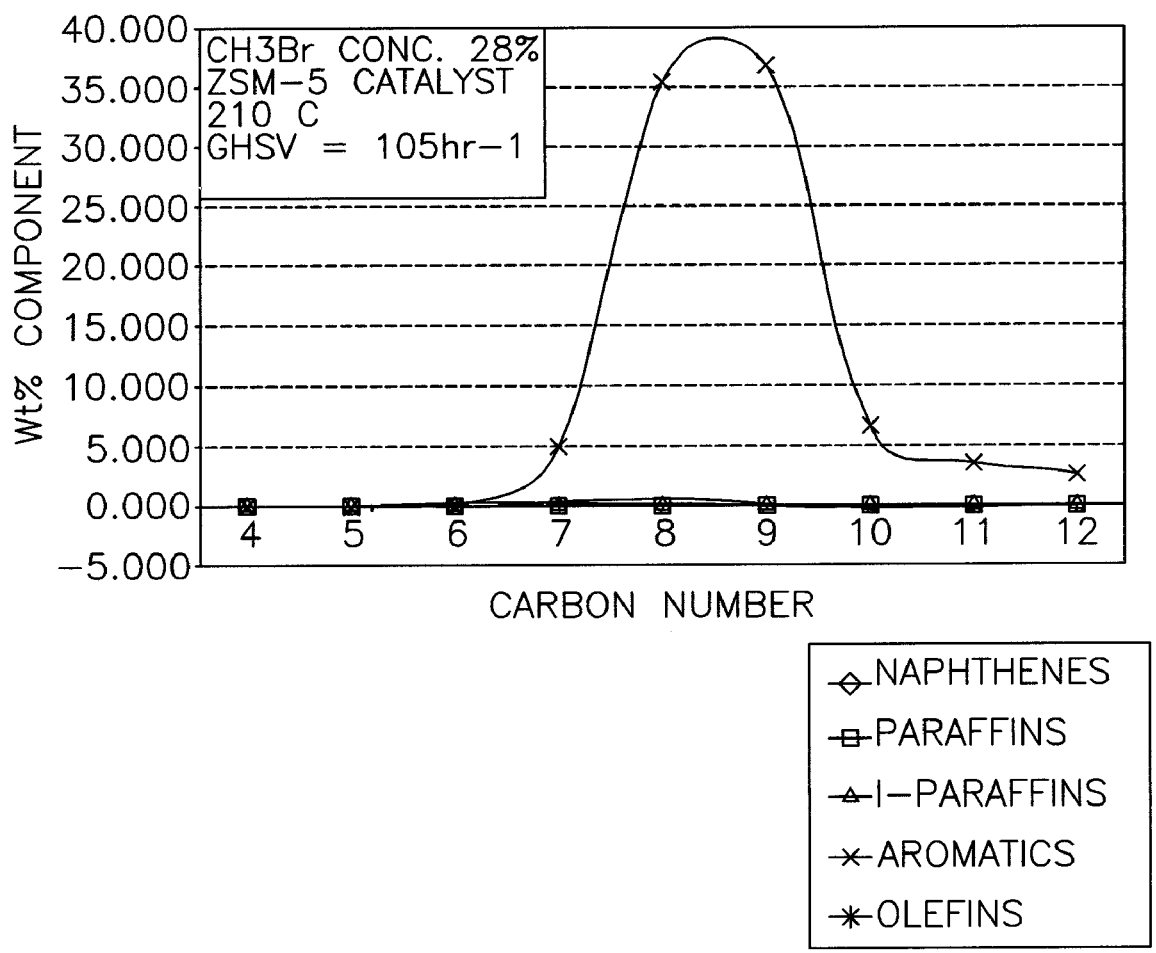
FIG. 8 is a graph of a PONA analysis of another typical condensed product sample of the present invention.

FIG. 7 and FIG. 8 illustrate two exemplary PONA analyses of two C$_6$+ liquid product samples that are recovered during two test runs with methyl bromide and methane reacting over ZSM-5 zeolite catalyst. These analyses show the substantially aromatic content of the C$_6$+ fractions produced.

EXAMPLE 3

Figure 4:
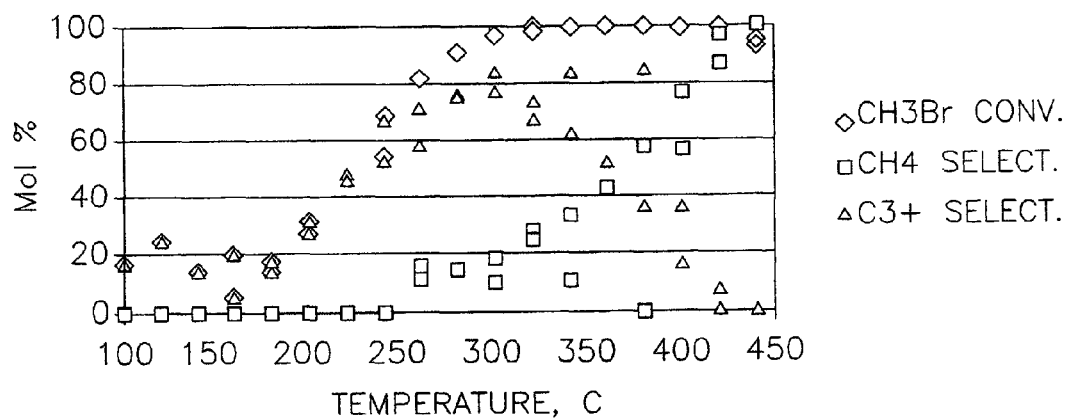
FIG. 4 is a graph of methyl bromide conversion and product selectivity for the oligimerization reaction of the process of the present invention as a function of temperature.

Methyl bromide is reacted over a ZSM-5 zeolite catalyst at a Gas Hourly Space Velocity (GHSV) of approximately 94 hr$^{-1}$ over a range of temperatures from about 100° C. to about 460° C. at approximately 2 bar pressure. As illustrated in FIG. 4, which is a graph of methyl bromide conversion and product selectivity for the oligimerization reaction as a function of temperature, methyl bromide conversion increases rapidly in the range of about 200° C. to about 350° C. Lower temperatures in the range of about 100° C. to about 250° C. favor selectivity towards higher molecular weight products however conversion is low. Higher temperatures in the range of about 250° C. to about 350° C. show higher conversions in the range of 50% to near 100%, however increasing selectivity to lower molecular weight products, in particular undesirable methane is observed. At higher temperatures above 350° C. selectivity to methane rapidly increases. At about 450° C., almost complete conversion to methane occurs.

EXAMPLE 4

Figure 5:
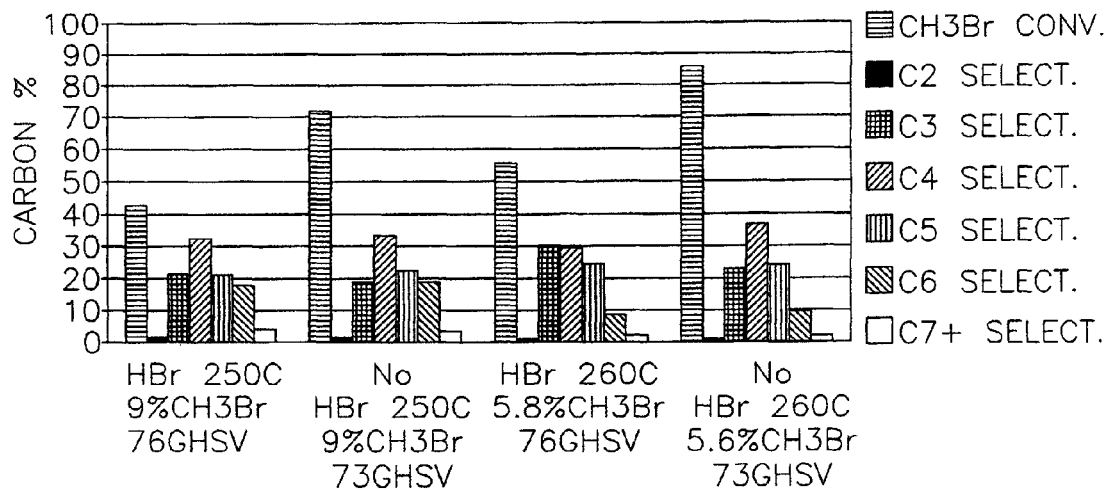
FIG. 5 is a graph comparing conversion and selectivity for the example of methyl bromide, dry hydrobromic acid and methane versus only methyl bromide plus methane.

Methyl bromide, hydrogen bromide and methane are reacted over a ZSM-5 zeolite catalyst at approximately 2 bar pressure at about 250° C. and also at about 260° C. at a GHSV of approximately 76 $hr^{-1}$. Comparison tests utilizing a mixture of only methyl bromide and methane without hydrogen bromide over the same ZSM-5 catalyst at approximately the same pressure at about 250° C. and at about 260° C. at a GHSV of approximately 73 $hr^{-1}$ were also run. FIG. 5, which is a graph that illustrates the comparative conversions and selectivities of several example test runs, shows only a very minor effect due to the presence of HBr on product selectivities. Because hydrobromic acid has only a minor effect on conversion and selectivity, it is not necessary to remove the hydrobromic acid generated in the bromination reaction step prior to the conversion reaction of the alkyl bromides, in which additional hydrobromic acid is formed in any case. Thus, the process can be substantially simplified.

EXAMPLE 5

Figure 6:
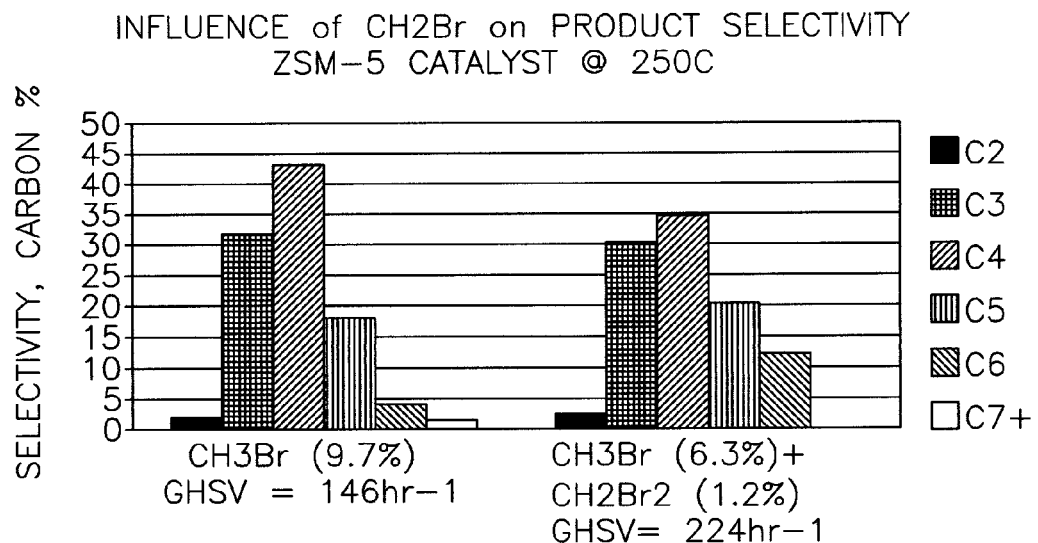
FIG. 6 is a graph of product selectivity from reaction of methyl bromide and dibromomethane vs. product selectivity from reaction of methyl bromide only.

Methyl bromide is reacted over a ZSM-5 zeolite catalyst at 230° C. Dibromomethane is added to the reactor. FIG. 6, which is a graph of product selectivity, indicates that reaction of methyl bromide and dibromomethane results in a shift in selectivity towards $C_5+$ products versus. methyl bromide alone. Thus, these results demonstrate that dibromomethane is also reactive and therefore very high selectivity to bromomethane in the bromination step is not required in the process of the present invention.

EXAMPLE 6

A mixture of 12.1 mol % methyl bromide and 2.8 mol % propyl bromide in methane are reacted over a ZSM-5 zeolite catalyst at 295 C and a GHSV of approximately 260 $hr^{-1}$. A methyl bromide conversion of approximately 86% and a propyl bromide conversion of approximately 98% is observed.

Thus, in accordance with all embodiments of the present invention, the metal bromide/metal hydroxide, metal oxybromide or metal oxide operates in a catalytic cycle allowing bromine to be easily recycled within the process. The metal bromide is readily oxidized by oxygen or air either in the aqueous phase or the vapor phase at temperatures in the range of about 100° C. to about 600° C. and most preferably in the range of about 120° C. to 180° C. to yield elemental bromine vapor and metal hydroxide, metal oxy-bromide or metal oxide. Operation at temperatures below about 180° C. is advantageous, thereby allowing the use of low-cost corrosion-resistant fluoropolymer-lined equipment. Hydrobromic acid is neutralized by reaction with the metal hydroxide or metal oxide yielding steam and the metal bromide.

The elemental bromine vapor and steam are condensed and easily separated in the liquid phase by simple physical separation, yielding substantially dry bromine. The absence of significant water allows selective bromination of alkanes, without production of $CO_2$ and the subsequent efficient and selective oligimerization and cyclization reactions of alkyl bromides to primarily propane and heavier products, the $C_5+$ fraction of which contains substantial branched alkanes and substituted aromatics. Byproduct hydrobromic acid vapor from the bromination and oligimerization reaction are readily dissolved into an aqueous phase and neutralized by the metal hydroxide or metal oxide species resulting from oxidation of the metal bromide.

The process of the present invention is less expensive than conventional processes since it operates at low pressures in the range of about 1 bar to about 30 bar and at relatively low temperatures in the range of about 20° C. to about 600° C. for the gas phase, and preferably about 20° C. to about 180° C. for the liquid phase. These operating conditions permit the use of less expensive equipment of relatively simple design that are constructed from readily available metal alloys for the gas phase and polymer-lined vessels, piping and pumps for the liquid phase. The process of the present invention is also more efficient because less energy is required for operation and the production of excessive carbon dioxide as an unwanted byproduct is minimized. The process is capable of directly producing a mixed hydrocarbon product containing various molecular-weight components in the liquefied petroleum gas (LPG) and motor gasoline fuels range that have substantial aromatic content thereby significantly increasing the octane value of the gasoline-range fuel components.

While the foregoing preferred embodiments of the invention have been described and shown, it is understood that the alternatives and modifications, such as those suggested and others, may be made thereto and fall within the scope of the invention.

I claim:

1. A hydrocarbon product consisting essentially of molecular weight components in the liquefied petroleum gas range and a $C_7+$ fraction that is in the motor gasoline hydrocarbon products range and consists essentially of substituted aromatics, said product produced by the process comprising:
flowing alkyl bromides into a reactor wherein said alkyl bromides are reacted over a catalyst to form said hydrocarbon product.

2. The hydrocarbon product of claim 1 wherein said catalyst is a synthetic crystalline alumino-silicate catalyst.

3. The hydrocarbon product of claim 2 wherein said crystalline alumino-silicate catalyst is a zeolite catalyst.

4. The hydrocarbon product of claim 3 wherein said zeolite catalyst is a ZSM-5 zeolite catalyst.

5. The hydrocarbon product of claim 4 wherein said ZSM-5 zeolite catalyst is modified with at least one modifying cation selected from lithium, potassium, cesium, Group IA alkaline metals, or Group IIA alkaline earth metals.

6. The hydrocarbon product of claim 5 wherein said ZSM-5 zeolite catalyst is modified by ion exchange with at least one cation selected from lithium, potassium, cesium, magnesium, calcium or barium.

7. The hydrocarbon product of claim 1 wherein said alkyl bromides are reacted over said catalyst in said reactor at a temperature from about 150° C. to about 400° C.

8. The hydrocarbon product of claim 7 wherein said temperature is from about 250° C. to about 350° C.

9. The hydrocarbon product of claim 1 wherein said alkyl bromides are reacted over said catalyst in said reactor at a pressure of about 1 to about 30 bar.

10. The hydrocarbon product of claim 1 wherein said components in the liquefied petroleum gas range includes propane.

11. The hydrocarbon product of claim 1 wherein said components in the liquefied petroleum gas range includes butane.

12. A hydrocarbon product consisting essentially of molecular weight components in the liquefied petroleum gas range and a $C_7+$ fraction that is in the motor gasoline hydrocarbon products range and consists essentially of substituted aromatics, said product produced by the process comprising:
- in a first reactor, reacting a gaseous feed containing lower molecular weight alkanes with bromine vapor to form alkyl bromides and hydrobromic acid; and
- in a second reactor, reacting said alkyl bromides in the presence of a catalyst and said hydrobromic acid to form said hydrocarbon product.

13. The hydrocarbon product of claim 12 wherein said catalyst is a synthetic crystalline alumino-silicate catalyst.

14. The hydrocarbon product of claim 12 wherein additional hydrobromic acid is formed in said second reactor.

15. The hydrocarbon product of claim 12 wherein said process further comprises:
- contacting said hydrobromic acid and said hydrocarbon product with water to remove said hydrobromic acid from said hydrocarbon product.

16. The hydrocarbon product of claim 15 wherein said water is an aqueous solution and said step of contacting comprises:
- removing said hydrobromic acid from said hydrocarbon product by neutralization reaction with said aqueous solution containing reaction products obtained by oxidizing an aqueous solution containing a metal bromide salt, the metal of said metal bromide salt being selected from Cu, Zn, Fe, Co, Ni, Mn, Ca or Mg bromide.

17. The hydrocarbon product of claim 15 wherein said step of contacting comprises:
- removing said hydrobromic acid from said hydrocarbon product by dissolution into said water forming a hydrobromic acid solution, said hydrobromic acid solution being neutralized by reaction with an aqueous solution containing a metal hydroxide obtained by oxidizing an aqueous metal bromide salt solution with oxygen, the metal of said metal bromide salt being selected from Cu, Zn, Fe, Co, Ni, Mn, Ca or Mg.

18. The hydrocarbon product of claim 15 wherein said step of contacting comprises removing said hydrobromic acid from said hydrocarbon product by dissolution into said water forming a hydrobromic acid solution, said process further comprising:
- vaporizing said hydrobromic acid solution and reacting said vaporized hydrobromic acid solution with a metal oxide, said metal oxide being obtained by oxidizing a metal bromide salt contained on a porous support, the metal of said metal bromide salt being selected from the group Cu, Zn, Fe, Co, Ni, Mn, Ca or Mg.

19. The hydrocarbon product of claim 15 wherein said hydrobromic acid is a vapor.

20. The hydrocarbon product of claim 15 wherein said process further comprises:
- converting said hydrobromic acid to bromine.

21. The hydrocarbon product of claim 20 wherein said process further comprises:
- recycling said bromine that is converted from said hydrobromic acid to said step of reacting with said gaseous feed, said bromine being recycled as a vapor.

22. The hydrocarbon product of claim 15 wherein said process further comprises:
- dehydrating said hydrocarbon product.

23. The hydrocarbon product of claim 14 wherein said process further comprises:
- contacting said hydrobromic acid, said additional hydrobromic acid and said hydrocarbon product with water to remove said hydrobromic acid and said additional hydrobromic acid from said hydrocarbon product.

24. The hydrocarbon product of claim 23 wherein said water is an aqueous solution and said step of contacting comprises:
- removing said hydrobromic acid and said additional hydrobromic acid from said hydrocarbon product by neutralization reaction with said aqueous solution containing reaction products obtained by oxidizing an aqueous solution containing a metal bromide salt, the metal of said metal bromide salt being selected from Cu, Zn, Fe, Co, Ni, Mn, Ca or Mg bromide.

25. The hydrocarbon product of claim 23 wherein said step of contacting comprises:
- removing said hydrobromic acid and said additional hydrobromic acid from said hydrocarbon product by dissolution into said water forming a hydrobromic acid solution, said hydrobromic acid solution being neutralized by reaction with an aqueous solution containing a metal hydroxide obtained by oxidizing an aqueous metal bromide salt solution with oxygen, the metal of said metal bromide salt being selected from Cu, Zn, Fe, Co, Ni, Mn, Ca or Mg.

26. The hydrocarbon product of claim 23 wherein said step of contacting comprises removing said hydrobromic acid and said additional hydrobromic acid from said hydrocarbon product by dissolution into said water forming a hydrobromic acid solution, said process further comprising:
- vaporizing said hydrobromic acid solution and reacting said vaporized hydrobromic acid solution with a metal oxide, said metal oxide being obtained by oxidizing a metal bromide salt contained on a porous support, the metal of said metal bromide salt being selected from the group Cu, Zn, Fe, Co, Ni, Mn, Ca or Mg.

27. The hydrocarbon product of claim 23 wherein each of said hydrobromic acid and said additional hydrobromic acid is a vapor.

28. The hydrocarbon product of claim 23 wherein said process further comprises:
- converting said hydrobromic acid and said additional hydrobromic acid to bromine.

29. The hydrocarbon product of claim 28 wherein said process further comprises:
- recycling said bromine that is converted from said hydrobromic acid and additional hydrobromic acid to said step of reacting with said gaseous feed, said bromine being recycled as a vapor.

30. The hydrocarbon product of claim 23 wherein said process further comprises:
- dehydrating said hydrocarbon product.

31. The hydrocarbon product of claim 12 wherein said components in the liquefied petroleum gas range includes propane.

32. The hydrocarbon product of claim 12 wherein said components in the liquefied petroleum gas range includes butane.

33. A hydrocarbon product consisting essentially of molecular weight components in the liquefied petroleum gas range and a $C_7+$ fraction that is in the motor gasoline hydrocarbon products range and consists essentially of substituted aromatics, said product produced by the process comprising:
- introducing a mixture comprising lower molecular weight gaseous alkanes and bromine vapor into a first reactor;
- withdrawing alkyl bromides and hydrobromic acid from said first reactor;
- flowing said alkyl bromides and said hydrobromic acid into a second reactor containing a catalyst; and
- withdrawing an effluent comprising said hydrobromic acid and said hydrocarbon product from said second reactor.

34. The hydrocarbon product of claim 33 wherein said components in the liquefied petroleum gas range includes propane.

35. The hydrocarbon product of claim 33 wherein said components in the liquefied petroleum gas range includes butane.

36. The hydrocarbon product of claim 33 wherein said hydrobromic acid is a vapor.

37. The hydrocarbon product of claim 33 wherein said catalyst is a synthetic crystalline alumino-silicate catalyst.

* * * * *